US012426987B2

(12) United States Patent
McNutt et al.

(10) Patent No.: US 12,426,987 B2
(45) Date of Patent: Sep. 30, 2025

(54) MEDICAL IMPLANT TRACKING SYSTEM

(71) Applicant: MedTrak Implant Tracking LLC, Gilbert, AZ (US)

(72) Inventors: Robert McNutt, Mesa, AZ (US); Venkatesh G. Ramaiah, Scottsdale, AZ (US); Briant Benson, Placerville, CA (US)

(73) Assignee: MEDTRAK, LLC, Little Rock, AR (US)

( * ) Notice: Subject to any disclaimer, the term of this patent is extended or adjusted under 35 U.S.C. 154(b) by 975 days.

(21) Appl. No.: 17/539,104

(22) Filed: Nov. 30, 2021

(65) Prior Publication Data

US 2022/0168065 A1 Jun. 2, 2022

Related U.S. Application Data

(60) Provisional application No. 63/120,146, filed on Dec. 1, 2020.

(51) Int. Cl.
*A61B 90/98* (2016.01)
*A61B 34/00* (2016.01)
*A61B 90/00* (2016.01)
*A61B 90/90* (2016.01)
*G06K 7/14* (2006.01)
(Continued)

(52) U.S. Cl.
CPC ............ *A61B 90/98* (2016.02); *G06K 7/1413* (2013.01); *G16H 40/63* (2018.01)

(58) Field of Classification Search
CPC .............. A61B 90/98; A61B 2034/256; A61B 2090/0814; A61B 90/90; G06K 7/1413; G16H 40/63; G16H 40/40
See application file for complete search history.

(56) References Cited

U.S. PATENT DOCUMENTS

2006/0089888 A1* 4/2006 Roger .................... G16H 40/20
705/28
2006/0235488 A1* 10/2006 Nycz ...................... A61B 90/90
607/2

(Continued)

FOREIGN PATENT DOCUMENTS

WO 200149368 A1 7/2001

*Primary Examiner* — Carrie R Dorna
*Assistant Examiner* — Joshua Daryl D Lannu
(74) *Attorney, Agent, or Firm* — Temmerman Law; Mathew J. Temmerman

(57) ABSTRACT

A system for identifying and tracking a plurality of implant devices. The system includes at least one communication device and a medical implant device tracking system. The medical implant device tracking system includes a processor on which is installed an implant device tracking application. The implant device tracking application enables the communication device to scan a unique device identifier (UDI) of the implant devices thereby recording a complete and accurate set of information about the implant devices. The medical implant device tracking system includes a database unit, an implant manufacturer access unit, a hospital access unit, a patient access unit, and a physician access unit. The implant device tracking application generates immediate notification of the recall status of the at least one implant device at the time of the implant device scanning thereby preventing the implantation of the recalled implant device in the patient's body.

20 Claims, 28 Drawing Sheets

(51) Int. Cl.
*G16H 40/40* (2018.01)
*G16H 40/63* (2018.01)

(56) References Cited

U.S. PATENT DOCUMENTS

| | | | |
|---|---|---|---|
| 2010/0161345 A1* | 6/2010 | Cain | G16H 40/20 |
| | | | 705/28 |
| 2010/0274591 A1 | 10/2010 | Wells | |
| 2016/0224761 A1* | 8/2016 | Dobkin | G06F 3/0484 |
| 2016/0374775 A1* | 12/2016 | Prpa | A61B 50/20 |
| | | | 705/3 |

* cited by examiner

358
Medical History

360
| Date | Patient |
|---|---|
| 01 MAY 2020 | Bill Jones |
| 18 FEB 2017 | Bill Jones |

[New Medical History Form] —362

FIG. 23A 364  366
Medications

| Date | Patient | Drug Name | Frequency | Discontinued |
|---|---|---|---|---|
| ~~06 MAR 2020~~ | ~~Bill Jones~~ | ~~Tylenol~~ | ~~2 / Day~~ | ~~Yes~~ ☒ |
| 18 JAN 2020 | Bill Jones | Advil | 1 / Day | No ☐ |

[New Medication]

FIG. 23B

370
Symptom Data Form

| Date | Patient |
|---|---|
| 01 MAY 2020 | Bill Jones |
| 18 FEB 2017 | Bill Jones |

[New Symptom Data Form] —368

MEDICAL IMPLANT TRACKING SYSTEM

RELATED APPLICATIONS

This application is a nonprovisional application claiming the benefit of provisional patent application 63/120,146, filed Dec. 1, 2020, the disclosure of which is incorporated herein in its entirety.

BACKGROUND OF THE DISCLOSURE

Technical Field of the Disclosure

The present invention relates generally to systems for tracking medical implant devices, and more particularly, to a medical implant device tracking system featuring an implant device tracking application designed to scan a unique device identifier (UDI) of the implant device thereby recording complete and accurate implant device information.

Description of the Related Art

Medical implant devices are widely used for diagnostic, therapeutic and rehabilitation purposes. These devices are partly or totally inserted into a human body by means of surgical or medical procedures. Examples of implantable devices include cardiac pacemakers, implantable cardiac defibrillators (ICDs), coronary stents, hip implants, interocular lenses and implantable insulin pumps. Some implants are designed to communicate wirelessly with external devices. These smart medical implant devices monitor and automatically deliver treatment in response to changes in the body. Tracking of the implant device enables to collect device information such that the implant device can be accurately identified and recalled if there is any health risk for the patient.

Several methods have been developed to track medical implant devices. Existing tracking methods are inefficient and wrought with multiple modes of failure. Some implantable devices are not even tracked anymore, for example peripheral and coronary vascular stents. A majority of medical device companies track implant devices utilizing duplicate forms which are filled out in a handwritten method by circulating nurses or device representatives. In this method, handwriting is not always legible and/or the forms may not include complete information. The information on these forms usually includes, but not limited to, the patient's personal information: name, date of birth, address, phone numbers, and possibly the patient's social security number, hospital MRN number, etc. These forms also include the physician's contact information and the facility or hospital's information. The nurse or device representative places stickers or labels located on the implant device boxes on each copy of these duplicate forms. These stickers or labels usually include device name, size or description, and a lot number of the implantable device. Sometimes, the number of available stickers may be inadequate for the entire device tracking forms and the hospital forms. Further, some of these stickers or labels may or may not include the company's name or the device expiration date. If the stickers or labels do not have this information, the nurses or device representatives may have to handwrite this information on the forms. Once the procedure is completed, the form is mailed to the company and to the hospital. Due to the advancement of electronic medical records, EMR, the hospital scans this paperwork into a PDF or similar format. However, this data is not farmable raw data, but an image of the handwritten form. Further, this information is only available if the hospital requests it from the device manufacturing company.

The Food and Drug Administration (FDA) has identified an inconsistency in medical implant device identification and tracking. According to FDA, most medical devices distributed in the United States carry a unique device identifier, or UDI. The UDI system has the potential to improve the quality of information in medical device adverse event reports, which help the FDA to identify product problems more quickly. This method allows better target recalls and improves patient safety. This device specific directive may also be adopted globally utilizing Global Unique Device Identification Database (GUDID). The smart phone or mobile computer pad can take a photo of the device labels which can be attached to the implant forms. The method for providing consistent information to the implant devices utilizing a barcode or some other mechanism is a step in the right direction. However, the tracking process is still dependent on the nurse or device representative filling out the necessary patient, hospital or facility or physician information. Due to the inefficient paper form method of tracking and even the inefficient PDF email method, there remains a need for one program or application to track and notify all entities of not just recalls but so much more.

Conventional implant device tracking methods do not connect FDA, hospital or facility, and physician to the patient. Further, these methods do not make the patients aware about the kind of implant they received or they cannot remember the date or year of the implant or they do not even remember which doctor or at which facility they had the surgery. Many times, due to the complexity of medical anatomy and medical terminology the patient has become a mal-informed historian.

Therefore, there is a need for an efficient and reliable system for identifying and tracking medical implant devices. Furthermore, such a system would allow a communication device to scan a unique device identifier (UDI) or similar barcode data of a medical implant device to record accurate and complete device information of the implant device on a database unit. Such a system would inform follow-up visit data to the physician and the patient. Moreover, such a system would allow viewing the location of the implant device in a patient's body. Such, a system would create different medical forms having highlighted fields which the nurse or the device representative cannot bypass thereby ensuring a complete and legible information gathering process. Further, such a system would prevent an implantation of a recalled implant device in a patient's body thereby improving the safety of the patient. The present embodiment overcomes shortcomings in the field by accomplishing these critical objectives.

SUMMARY OF THE DISCLOSURE

To minimize the limitations found in the prior art, and to minimize other limitations that will be apparent upon the reading of the specification, the present disclosure provides a system for identifying and tracking a plurality of implant devices. The system includes at least one communication device and a medical implant device tracking system.

The at least one communication device is operatively coupled with at least one of the plurality of implant devices. The medical implant device tracking system is in communication with the at least one communication device and the plurality of implant devices via a network. The medical implant device tracking system includes an implant tracking server residing on a central computer having a processor on which is installed an implant device tracking application and coupled with a memory unit integrated with a central database. The implant device tracking application enables the communication device to scan a unique device identifier (UDI) of the at least one of the plurality of implant devices thereby recording a complete and accurate set of information about the at least one of the plurality of implant devices. The scanning of the implant device alerts a nurse or a device representative when the implant device has expired or on recall. This function prevents improper devices from being implanted in a patient or even placed on an operating field.

In the preferred embodiment, the at least one communication device is selected from a group consisting of: a cellular telephone, a smartphone, a wireless-enabled personal digital assistant, a tablet, a personal computer, a laptop and/or a mobile device. The network is a secured data communication network selected from at least one of but not limited to: Internet, a local area network (LAN), a wide area network (WAN), wired Ethernet, wireless Ethernet and cellular wireless network.

The medical implant device tracking system includes a database unit, an implant manufacturer access unit, a hospital access unit, a physician access unit, and a patient access unit. The database unit is configured to store and manage information related to the plurality of implant devices in an implant device database and logic to manage and route data to the communication device.

The implant manufacturer access unit includes a data farming/collecting and reporting module for managing a plurality of manufacturer records. A manufacturer recall management module in the implant manufacturer access unit manages and creates a recall list having a plurality of recall notices. The manufacturer recall management module manages details regarding the placement of the at least one implant device in the patient's body and the associated recall information of the at least one implant device. This function of the manufacturer recall management module enables the matching of the recalled implant device/a device lot number with the at least one implant device of the patient.

A manufacturer recall notice module enables the manufacturer to send at least one of the plurality of recall notices to a physician and a hospital. A manufacturer acknowledgement module allows the manufacturer to receive and store the acknowledge confirmation notice from the physician and the hospital in a sent recall acknowledge list. A recalled device tracking module enables the implant manufacturer to view the location and the status of the plurality of implant devices related to a recall of the at least one implant device utilizing the device lot number. The recalled device tracking module is designed to display whether a message has been sent, has acknowledged, has a pending response and to enable the implant manufacturer to view the most critical device recalls requiring attention.

The system utilizes an acknowledge message mechanism that allows the patient, the physician, the hospital, and the implant manufacturer to acknowledge a plurality of messages having immutable and traceable records. Based on this acknowledge message mechanism, the messages that require tracking and reporting arrive with an acknowledge button. Once selected, the user is not able to ignore that message without acknowledging. Upon acknowledging, the sender receives a confirmation of that acknowledgment message.

A manufacturer recall device alert module allows the manufacturer to receive an immediate notification of the recall status of the at least one implant device generated by the implant device tracking application at the time of the implant device scanning. This immediate notification prevents the implantation of the recalled implant device in the patient's body during a medical procedure. The immediate notification may be a warning signal like "Recalled Device. Cannot be Used in Procedure". The generation of the warning signal improves the safety of the patient.

The manufacturer implant access unit includes a manufacturer procedure record access module to access at least one procedure record of the patient whose procedure included same manufacturer medical device utilizing a searchable list of procedure records and to create new procedure records. The list of procedure records includes but is not limited to hospital records, device records, patient records and physician records.

A manufacturer device placement module allows the manufacturer to view the location of the at least one implant device in the patient's body. Here, an implant device icon is positioned on a standard image of the patient's body by the physician during a medical procedure to portray the location of a device implanted on a Patient's body. The physician, the hospital and the patient also can view the implant device's location in the patient's body.

A manufacturer outgoing message module manages communication and outgoing messages from an implant manufacturer. The manufacturer outgoing message module displays a list of issued messages by the manufacturer. The manufacturer incoming message module is configured to manage incoming messages from the physician and the hospital.

A survey management module performs at least one implant device survey. A survey template record includes a group of searchable fields to enter search criteria into which a list of survey records is displayed. The survey record list includes survey description. A survey result handling module reviews survey responses from the at least one implant device survey.

A company information update module updates information associated with the implant manufacturer or a company. The company information update module includes different methods to identify and save a list of all implant devices. The company information update module enables the user to provide additional details, if any.

The implant manufacturer access unit provides instructions for use (IFU) restrictions and requirements, the recall notices and device information to a user selected implant device.

The hospital access unit includes a hospital recall notice module that enables the hospital to receive the at least one of the plurality of recall notices from the implant manufacturer. A hospital acknowledgement module allows the hospital to send the acknowledge confirmation notice to the implant manufacturer. Further, a hospital recall forward module in the hospital access unit forwards the at least one of the plurality of recall notices to the patient. The implant device tracking application automatically captures a list of recall-status of the patient having the recalled implant device and the device lot number and automatically pushes the at least one of the plurality of recall notices in the patient access unit.

A hospital device placement module allows a hospital staff to view the location of the at least one implant device in the patient's body. The hospital staff may be an administrator or a nurse. A hospital recall device alert module allows the hospital staff to receive the immediate notification of the recall status of the implant device thereby preventing the implantation of the recalled implant device in the patient's body during the medical procedure.

A hospital incoming message module is configured to manage incoming messages received by the hospital. The hospital inbound message may include device tracking forms, recall messages, field safety notices, or direct messages controlled by the database unit. A hospital outgoing message module manages an implant device communication section and the outgoing messages to the communication device. The outgoing messages provide information regarding health checks or health advertisements to a patient retention module. A patient information access module is configured to access patient information utilizing a searchable list of patients. The hospital access unit further includes a procedure record access module to access at least one procedure record of the patient utilizing a searchable list of procedure records and to create new procedure records. The searchable list of patients and the list of procedure records are stored in the implant device database. The list of procedure records includes but is not limited to device records, patient records and physician records. The hospital access unit provides details such as instructions for use (IFU) restrictions and requirements, the recall notices and device information to the user selected implant device.

The physician access unit is operatively coupled with the plurality of implant devices. The physician access unit includes a patient information module to view an existing patient record and to create a new patient record. The patient information module enables to search patient records utilizing multiple search fields.

The physician access unit includes a procedure record module. The procedure record includes a device record, a patient record, a hospital record, and a physician record. The procedure record module is designed to view an existing procedure record and to create a new procedure record. A device master data module is designed to access records of the plurality of implant devices. The device master data module includes various methods to identify and save a list of all implant devices.

A physician recall notice module in the physician access unit enables the physician to receive the at least one of the plurality of recall notices from the implant manufacturer. A physician acknowledgement module allows the physician to send the acknowledge confirmation notice to the implant manufacturer. Further, a physician recall forward module in the physician access unit forwards the at least one of the plurality of recall notices to the patient. The implant device tracking application automatically captures a list of recall-status of the patient having the recalled implant device and the device lot number and automatically pushes the at least one of the plurality of recall notices in the patient access unit.

A physician device placement module allows the physician to position the implant device icon on the image of the patient's body during a medical procedure thereby displaying the location of the at least one implant device in the patient's body. A physician recall device alert module allows the physician to receive the immediate notification of the recall status of the at least one implant device thereby preventing the implantation of the recalled implant device in the patient's body during a medical procedure.

A physician contact information module enables the physician to store contact information of the physician in the database unit. An emergency physician contact module is designed to store emergency details of the physician in the database unit. The physician access unit includes a physician health check-up module to store a list of health checks and follow-up visit data in the database unit.

A physician incoming message module is designed to create a list of physician incoming notices. The list of physician incoming notices notifies hospital appointment reminders and indicates the status of each physician incoming notice to the user such as whether the notice is acknowledged or not. Further, the physician incoming notice module notifies date/time at which the acknowledgement is captured. A physician outgoing message module manages outgoing messages and the implant device communication section.

A physician information update module updates contact information of the physician. The physician access unit provides IFU restrictions and requirements, the recall notices and device information to the user selected implant device.

The patient access unit includes a device ID card module to provide an electronic wallet of a medical device ID card to the patient that allows the patient to store their critical medical device identification information in a password protected and traceable application. In the preferred embodiment, the medical device ID card is viewable and accessible to the patient at the moment a medical procedure is approved/completed by the physician. The medical device ID card stores the medical device identification information in an electronic format. Further, the device ID card module allows the patient to access the medical device ID card from anywhere and at any time as desired utilizing the protected and traceable application.

A patient recall module enables the patient to receive the at least one of the plurality of recall notices forwarded by the physician and the hospital. A patient device placement module allows the patient to view the location of the at least one implant device in the patient's body.

A medical history module is provided to store information regarding patient medical history, disease symptoms and medications in the database unit. A medical device procedure tracking module in the patient access unit enables the patients to access their device information, recall information, procedure notes, procedure images and the location of the implant device on an image of the patient body. A patient contact information module enables the system to store contact information of patients in the database unit.

A patient incoming notice module notifies of hospital appointment reminders and the status of each notice to the patient such as whether the notice is acknowledged or not. Further, the incoming notice module notifies date/time at which the acknowledgement was captured. A list of incoming procedure follow-up notices is sent to the patient by the physician. The incoming notices notify the user that the messages are waiting to be viewed and indicate the number of messages which are not yet viewed.

An emergency contact module stores emergency contact details of the patient in the database unit. The patient access unit includes a health checks and follow-up module to store a list of health checks and follow-up visit data in the database unit. Initial procedure record of a patient supplies a first date. The health checks and follow-up visit data provide an appointment history of the patient for providing to a new doctor. The patient access unit provides procedure record notes, IFU restrictions and requirements, the recall notices and device information to the user selected implant device.

The process for creating and managing the recall notices in the preferred embodiment can be summarized as: the manufacturer selects the at least one implant device and the device lot number. Then, the manufacturer creates a recall notice and attaches a recall date to the recall notice. The device lot number for all procedures with that device as well as shelved products is searched in the implant device database connected to the hospital access unit, the physician access unit, or the implant manufacturer access unit. The recall notices are automatically routed to the corresponding physician and the hospital utilizing the secured notification process of the medical implant device tracking system. The physician and the hospital receive the recall notice and send an acknowledge confirmation notice to the manufacturer. The manufacturer receives the acknowledge confirmation notice in the sent recall acknowledge list. The hospital or the physician forwards the recall notice to the patient. The implant device tracking application automatically captures all patients with the recalled device and the device lot number and the recall notice is automatically pushed to the patient access unit.

The implant device tracking system provides a feedback form to the patients to enter their recent experience with the physician, medical procedure, and the implant device. The feedback form submitted by the patients enables to improve the performance of the medical implant device tracking system.

The preferred medical implant device tracking system provides an efficient and consistent way to track the plurality of implant devices thereby improving safety of the patients. The medical implant device tracking system acts as an organizer for a patient's medical and dental requirements. The medical implant device tracking system facilitates submission of implant device tracking forms or electronic implant cards to the Food and Drug Administration (FDA), device manufacturer, hospital or facility, physician, and the patient. These electronic implant cards include the implant device's instructions for use (IFU) restrictions and requirements which allows the patient and others to check magnetic resonance imaging (MRI) compatibility of the device, suggested follow-up, and more features. Further, the implant device tracking application assists the physician in keeping track of all his patients so that no patient is lost to follow-up. The implant device tracking system automatically generates a data tracking form (DTF) at the moment when the medical procedure is approved/closed by the physician. The DTF is automatically routed to the associated implant device manufacturers relating to the plurality of medical devices of said procedure. The medical implant device tracking system can be expanded to assist in recording and tracking a patient's medications and dosages. Moreover, information stored in the database unit of this implant tracking system is secured utilizing specific biomarkers or passwords which allow only authorized persons such as patient, physician, hospital or facility, company, or FDA to access the recorded information of the implant device.

It is a first objective of the present invention to provide a medical implant device tracking system for identifying and tracking a plurality of implant devices.

A second objective of the present invention is to provide a medical implant device tracking system that enables to scan a unique device identifier (UDI) of an implant device thereby recording complete and accurate information of that device.

A third objective of the present invention is to provide a medical implant device tracking system that enables physicians and medical professionals to easily access a patient's medical history.

A fourth objective of the present invention is to provide a medical implant device tracking system featuring an implant device tracking application that can be programmed to notify of a follow-up visit to the physician and the patient.

A fifth objective of the present invention is to provide a medical implant device tracking system designed to create different medical forms having highlighted fields which the nurse or the device representative cannot bypass thereby ensuring a complete and legible information gathering process.

A sixth objective of the present invention is to provide a medical implant device tracking system that allows more accurate reporting, reviewing and analysis of adverse event reports so that the implant devices having issues can be identified and corrected more quickly.

A seventh objective of the present invention is to provide a medical implant device tracking system that allows one to position an implant device icon on an image of a patient's body that enables patients, healthcare professionals, and manufacturers to view the location of the implant device in the patient's body.

An eighth objective of the present invention is to provide a medical implant device tracking system that generates an immediate notification message to a physician, a hospital, and an implant device manufacturer to prevent an implantation of a recalled implant device in a patient's body thereby improving the safety of the patient.

A ninth objective of the present invention is to provide a medical implant device tracking system that provides an electronic wallet of a medical device ID card to a patient that allows the patient to store his or her critical medical device identification information in a password protected and traceable application.

A tenth objective of the present invention is to provide a medical implant device tracking system that utilizes an acknowledgement message mechanism for allowing a patient, a physician, a hospital, and an implant manufacturer to acknowledge a plurality of messages having immutable and traceable records.

Another objective of the present invention is to provide a medical implant device tracking system that reduces medical errors thereby enabling healthcare professionals to identify a medical implant device more rapidly and precisely and obtain important information regarding the characteristics of that device.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention. Thus, the drawings are generalized in form in the interest of clarity and conciseness.

FIG. 6 illustrates a screenshot of a list of procedure records of the patients accessed by the implant device manufacturer utilizing a manufacturer procedure record access module in the implant manufacturer access unit in accordance with the preferred embodiment of the present invention;

FIG. 11 illustrates a screenshot showing details of the plurality of implant devices viewed by a hospital staff through a communication device in accordance with the preferred embodiment of the present invention;

FIG. 15 illustrates a screenshot showing details of the plurality of implant devices viewed by the physician through the communication device in accordance with the preferred embodiment of the present invention;

FIG. 20 illustrates a screenshot showing details of the physician in accordance with the preferred embodiment of the present invention;

FIG. 23A illustrates a medical history form for the patient created by a medical history module in the patient access unit in accordance with the preferred embodiment of the present invention;

FIG. 23B illustrates a medication details form created by the medical history module in the patient access unit in accordance with the preferred embodiment of the present invention;

FIG. 23C illustrates a disease symptom information form created by the medical history module in the patient access unit in accordance with the preferred embodiment of the present invention;

FIG. 28 illustrates a feedback form provided to the patient in accordance with the preferred embodiment of the present invention.

DETAILED DESCRIPTION

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about" means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas" "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
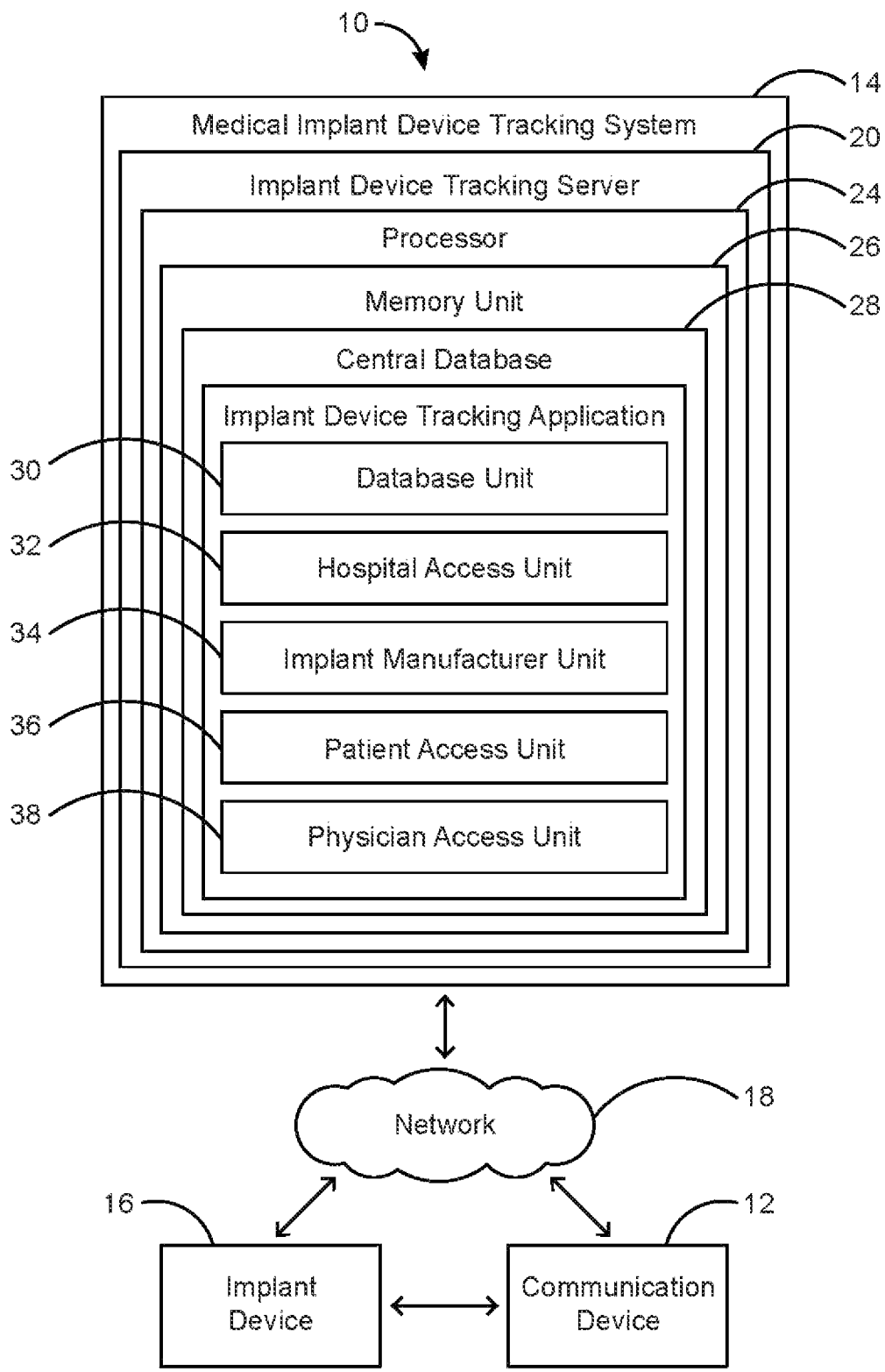
FIG. 1 illustrates a block diagram of a system for identifying and tracking a plurality of implant devices in accordance with the preferred embodiment of the present invention.

Referring to FIG. 1, a system 10 for identifying and tracking a plurality of implant devices 16 is illustrated. The system 10 includes at least one communication device 12 and a medical implant device tracking system 14. The at least one communication device 12 is operatively coupled with at least one of the plurality of implant devices 16. The medical implant device tracking system 14 is in communication with the at least one communication device 12 and the plurality of implant devices via a network 18. The medical implant device tracking system 14 includes an implant tracking server 20 residing on a central computer having a processor 24 on which is installed an implant device tracking application and coupled with a memory unit 26 integrated with a central database 28. The implant device tracking application enables the at least one communication device 12 to scan a unique device identifier (UDI) of the at least one of the plurality of implant devices 16 thereby recording a complete and accurate set of information about the at least one of the plurality of implant devices 16. The scanning of the implant device 16 alerts a nurse or the device representative when the implant device 16 has expired or on recall. This function prevents improper devices from being implanted in a patient or even placed on an operating field.

In the preferred embodiment, the at least one communication device 12 is selected from a group consisting of: a cellular telephone, a smartphone, a wireless-enabled personal digital assistant, a tablet, a personal computer, a laptop and/or a mobile device. The network 18 is a secured data communication network selected from at least one of but not limited to: Internet, a local area network (LAN), a wide area network (WAN), wired Ethernet, wireless Ethernet and cellular wireless network.

The medical implant device tracking system 14 includes a database unit 30, an implant manufacturer access unit 34, a hospital access unit 32, a patient access unit 36 and a physician access unit 38. The database unit 30 is configured to store and manage information related to the plurality of implant devices 16 in an implant device database and logic to manage and route data to the at least one communication device.

Figure 2:
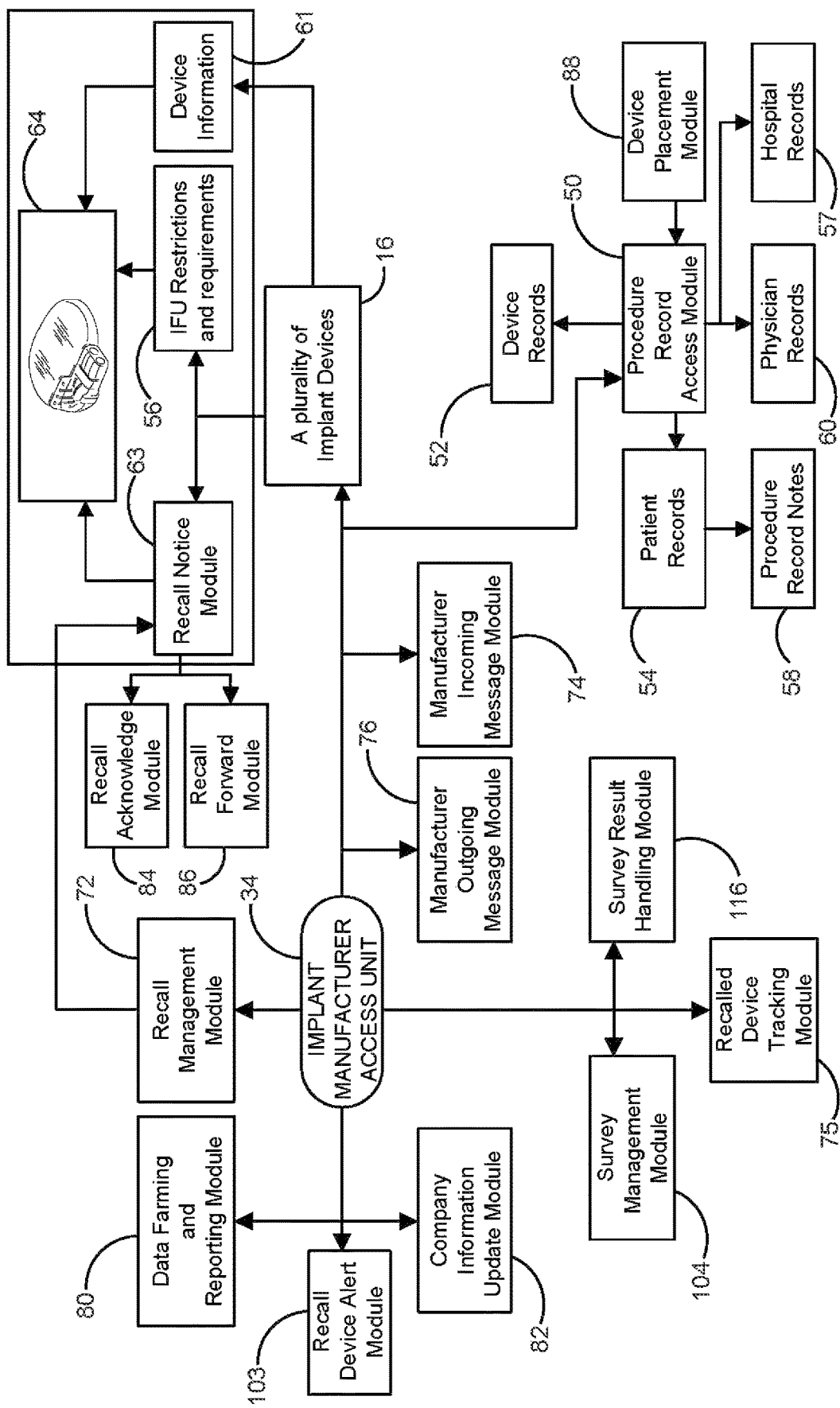
FIG. 2 illustrates a block diagram of an implant manufacturer access unit of a medical implant device tracking system in accordance with the preferred embodiment of the present invention.

As shown in FIG. 2, the implant manufacturer access unit 34 includes a data farming and reporting module 80 for collecting and managing a plurality of manufacturer records. A manufacturer recall management module 72 in the implant manufacturer access unit 34 manages and creates a recall list having a plurality of recall notices 236 (see FIG. 5). The manufacturer recall management 72 manages details regarding the placement of the at least one implant device 16 in the patient's body and the associated recall information of the at least one implant device 16. This function of the manufacturer recall management module 72 enables the matching of the recalled implant device/a device lot number 210 (see FIG. 4) with the at least one implant device 16 of the patient.

Figure 3:
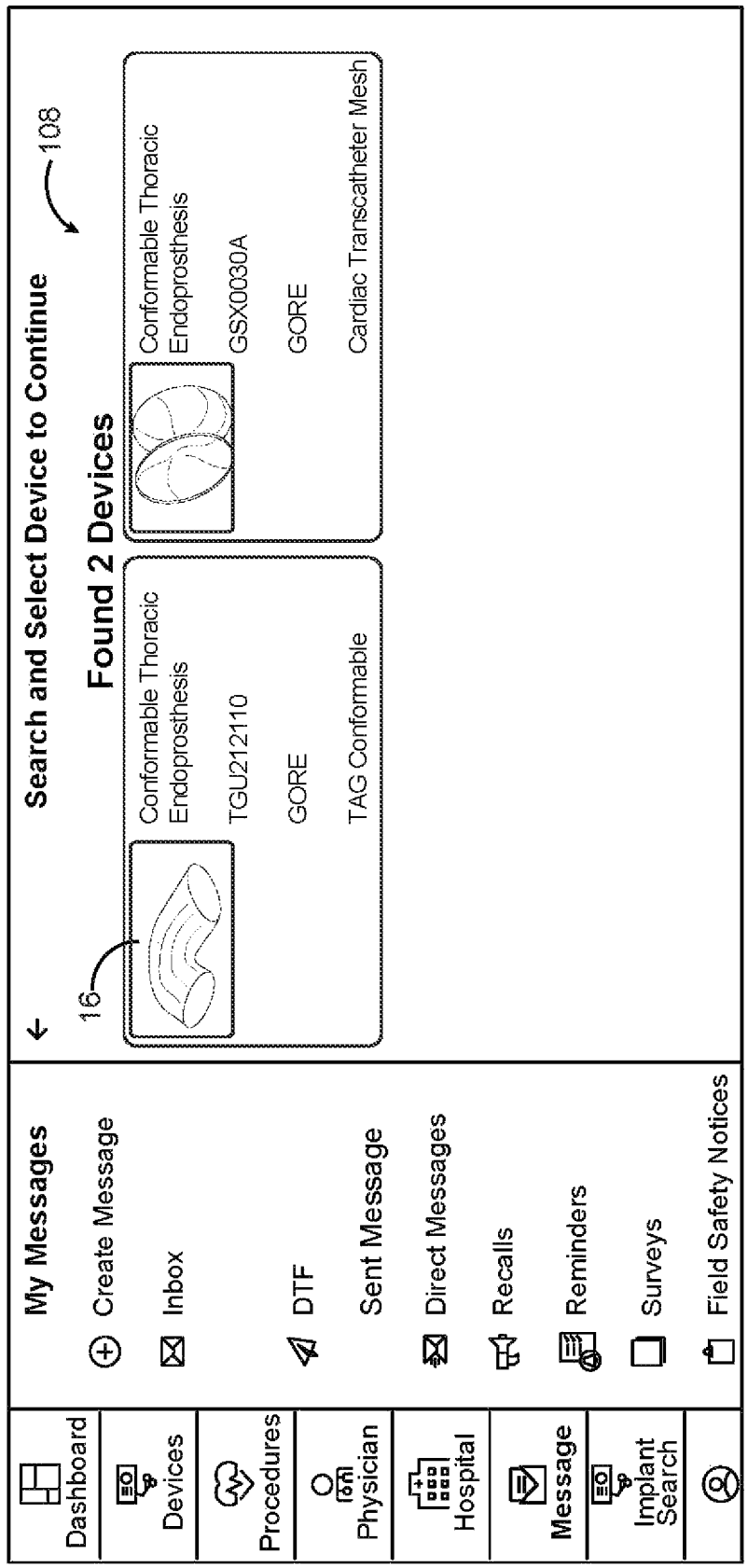
FIG. 3 illustrates a screenshot showing details of the plurality of implant devices displayed to an implant device manufacturer in accordance with the preferred embodiment of the present invention.
Figure 4:
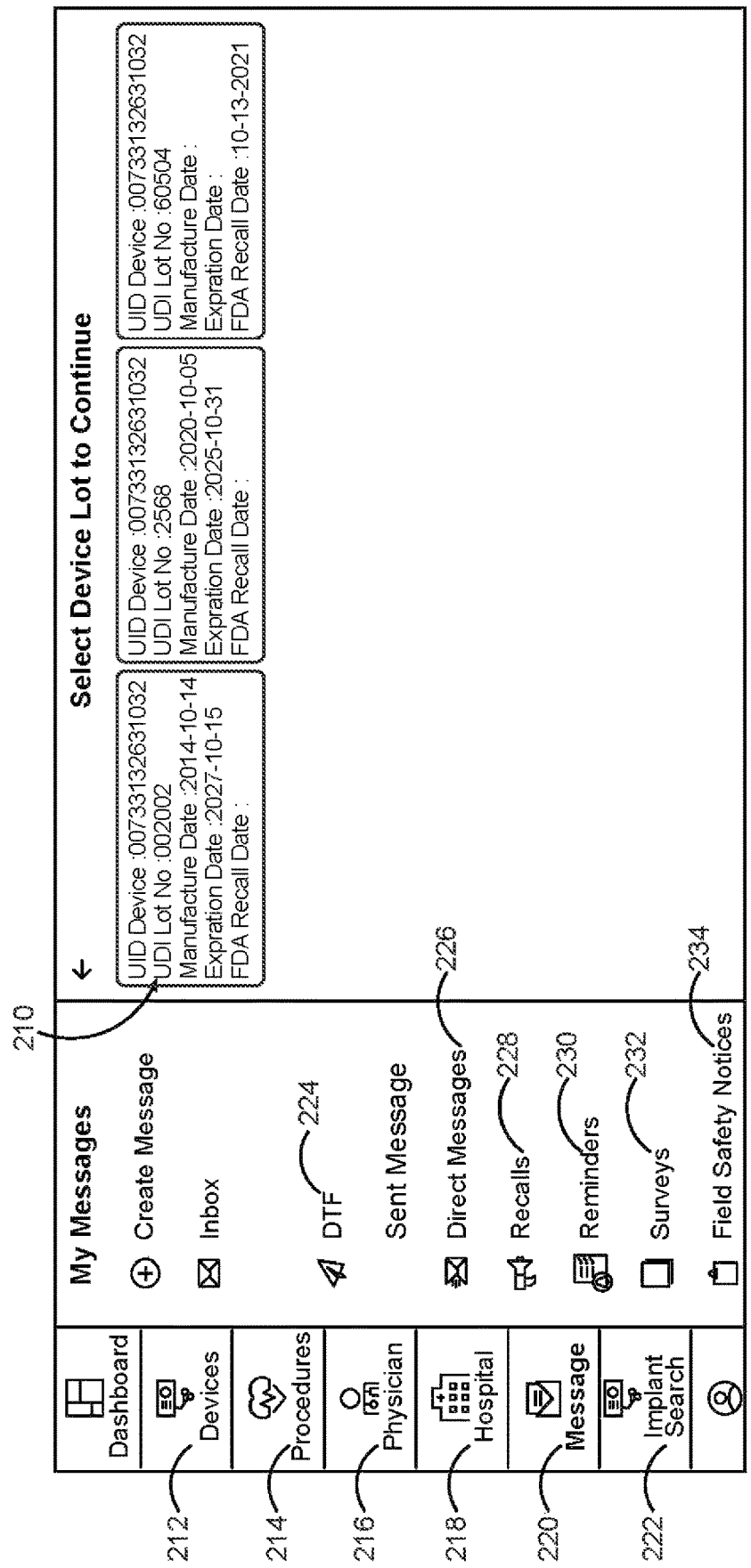
FIG. 4 illustrates a screenshot showing device lot numbers of the plurality of implant devices in accordance with the preferred embodiment of the present invention.

As shown in FIG. 3, the manufacturer can search for the plurality of implant devices 16. A device search result 108 showing details of a set of implant devices 16 is displayed to the manufacturer. When the manufacturer selects the at least one implant device 16 from the device search result 108, he will be navigated to another webpage as shown in FIG. 4 where the manufacturer can view device lot numbers 210 associated with the implant devices 16. With an advanced search capability provided by the medical implant device tracking system 14, the manufacturer can view additional details of the implant device 16 such as UID number, Manufacture Date, Expiration Date and FDA Recall Date corresponding to each implant device 16. The manufacturer selects at least one device lot number 210 to continue his desired function. The manufacturer can perform several functions by selecting options such as Devices 212, Procedures 214, Physician 216, Hospital 218, Messages 220, and Implant Search 222. Further, the manufacturer can create new messages relating to device tracking form (DTF) 224, Direct Messages 226, Recalls 228, Reminder 230, Surveys 232, and Field safety notices 234.

Figure 5:
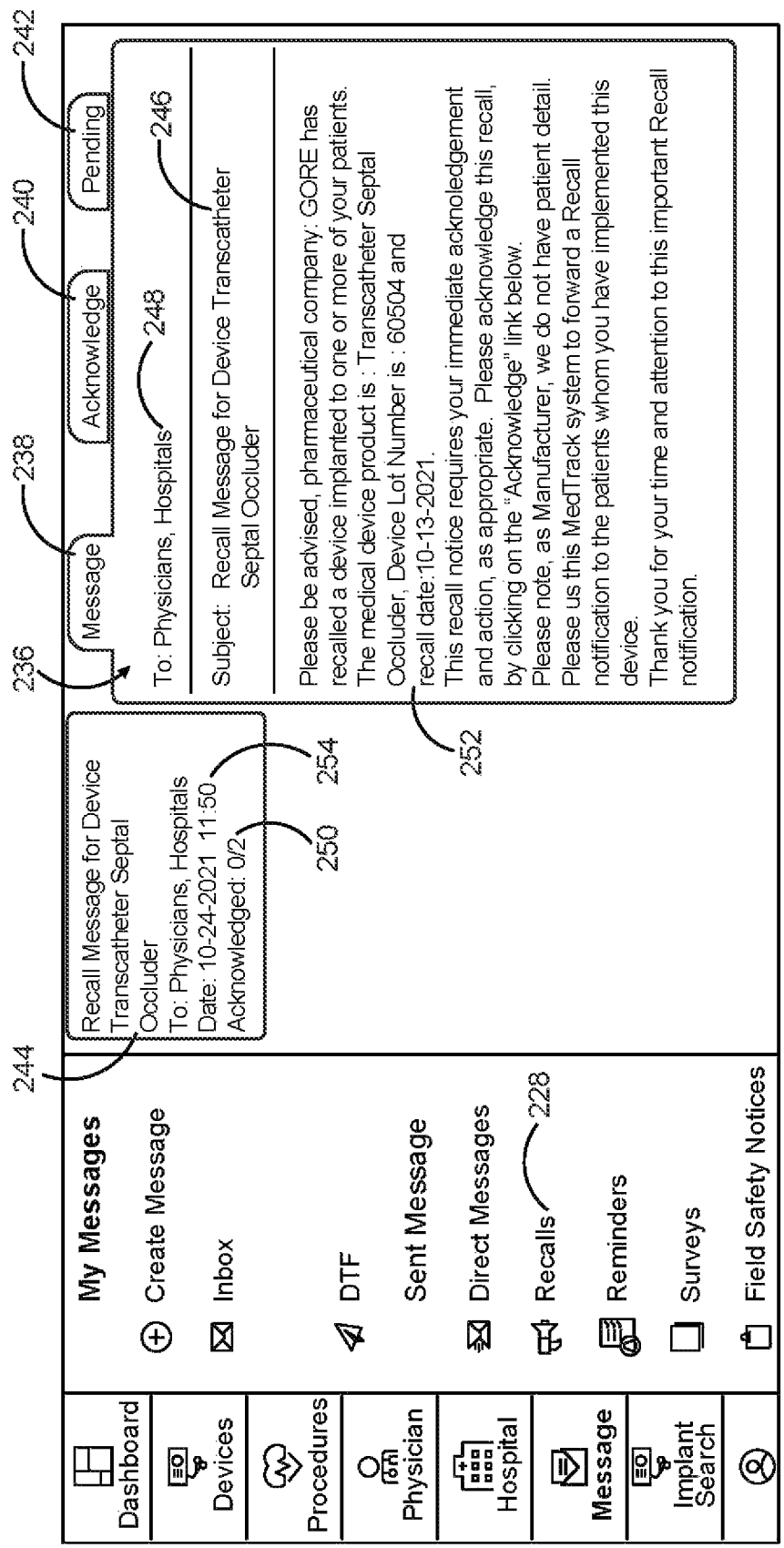
FIG. 5 illustrates a screenshot of a recall notice sent by the implant device manufacturer to a physician and a hospital in accordance with the preferred embodiment of the present invention.

The implant manufacturer access unit 34 includes a manufacturer recall notice module 63 that enables the manufacturer to send at least one of the plurality of recall notices 236 to a physician and a hospital. FIG. 5 shows a screenshot of a recall notice 236 sent by the manufacturer of the implant device 16 to the physician and the hospital. By selecting the "Recalls" option 228, the manufacturer can view the status of all recall notices 236. A manufacturer acknowledgement module 84 allows the manufacturer to receive and store an acknowledge confirmation notice from the physician and the hospital in a sent recall acknowledge list. In the preferred embodiment, once the implant device 16 and the device lot number 210 have been selected by the manufacturer as shown in FIG. 3 and FIG. 4 respectively, the medical implant device tracking system 14 prompts for a recall date. Then, the message template for the device recall will be displayed to the manufacturer as shown in FIG. 5. The recall notice 236 includes name 244 of the implant device 16, message subject 246, message body 252, date 254, recipient list 248 and recipient's acknowledgement status 250. Thereafter, the manufacturer sends the recall notice 236 to the corresponding physician and the hospital.

As shown in FIG. 5, the "Message" tab 238 allows the manufacturer to create and send the plurality of recall notices 236 to the physician and the hospital. The "Acknowledge" tab 240 allows the manufacturer to view the acknowledge confirmation notice from the physician and the hospital. The "Pending" tab 242 allows the manufacturer to find pending recall notices, if any. In the preferred embodiment, the system 14 utilizes an acknowledge message mechanism that allows the patient, the physician, the hospital, and the manufacturer to acknowledge a plurality of messages having immutable and traceable records. Based on this acknowledge message mechanism, the messages that require tracking and reporting arrive with an acknowledge button. Once selected, the user is not able to ignore that message without acknowledging. Once acknowledged, the sender receives a confirmation of that acknowledgment message. This feature of the system 14 replaces the need for a wet signature.

A manufacturer recall device alert module 103 in the manufacturer implant access unit 34 allows the manufacturer to receive an immediate notification of the recall status of the at least one implant device 16 generated by the implant device tracking application at the time of an implant device scanning. The immediate notification may be a warning signal like "Recalled Device. Cannot be Used in Procedure". This warning message prevents the implantation of the recalled implant device in the patient's body during a medical procedure thereby providing improved protection to the patients.

A recalled device tracking module 75 as shown in FIG. 2 enables the implant manufacturer to view the location and the status of the plurality of implant devices 16 related to a recall of the implant device 16 utilizing the device lot number 210. The recalled device tracking module 75 is designed to display whether a message has been sent, has acknowledged, has a pending response and to enable the manufacturer to view the most critical device recalls requiring attention.

Figure 6:
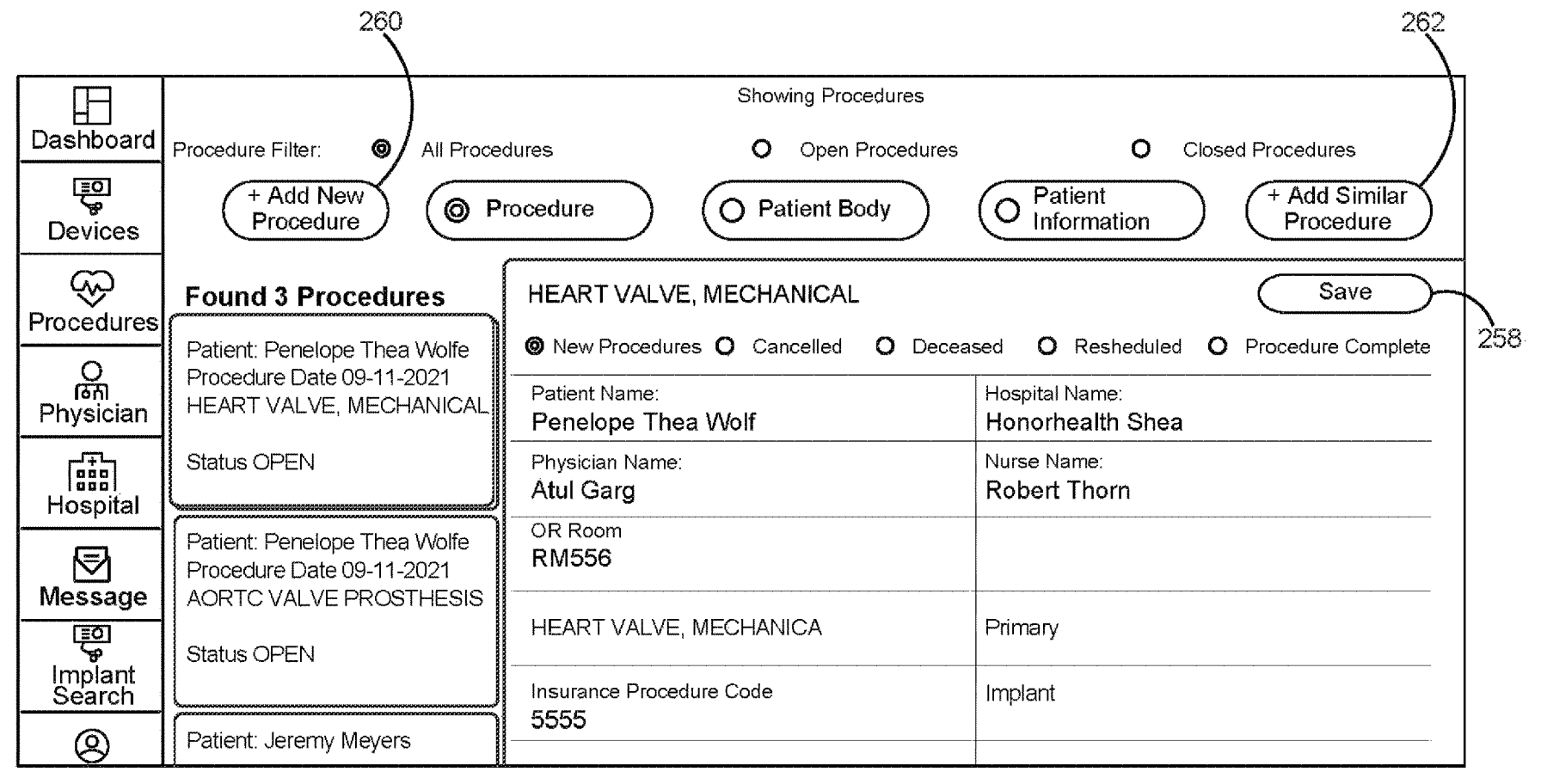

The manufacturer access unit 34 includes a manufacturer procedure record access module 50 to access at least one procedure record of a patient whose procedure included same manufacturer implant device utilizing a searchable list of procedure records and to create new procedure records. The list of procedure records includes but is not limited to hospital records 57, device records 52, patient records 54 and physician records 60. The patient records include procedure record notes 58. As shown in FIG. 6, the manufacturer can view each procedure record by selecting options such as All Procedures, Open Procedures and Closed Procedures. Further, the manufacturer can view additional details of the patient by selecting the options Patient Body and Patient Information. The manufacturer creates a new procedure record by selecting "Add New Procedure" 260. Further, the manufacturer can add similar medical procedure by selecting "Add Similar procedure" 262. By selecting the "Save" 258 button, the newly added procedure record can be saved to the implant device database. As shown in FIG. 6, when "All Procedure" option is selected, information regarding all medical procedures is displayed. The manufacturer can view additional details regarding the procedure such as Procedure Date, Procedure Name, Procedure Status, Patient Name, Hospital Name, Physician Name, Nurse Name, and Insurance Procedure Code.

Figure 7:
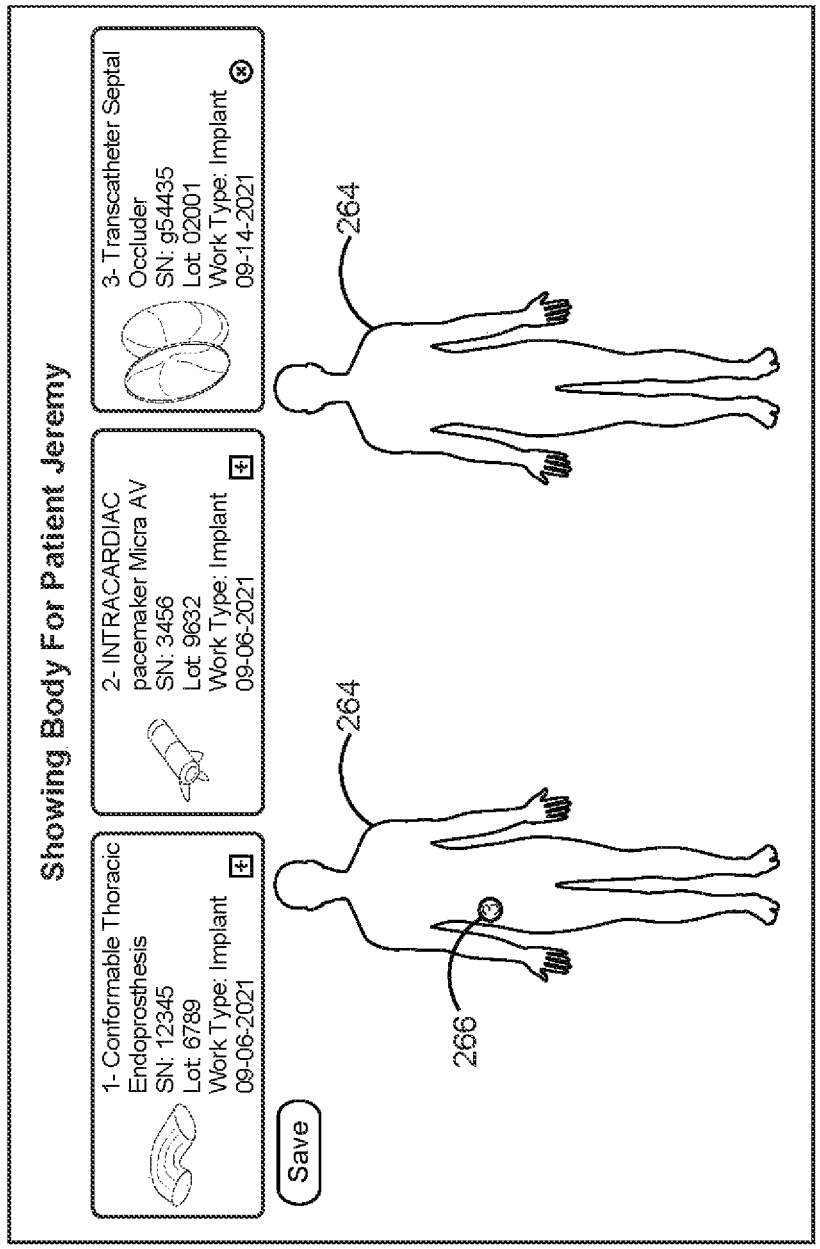
FIG. 7 illustrates a screenshot of an implant device icon positioned on a standard image of a patient's body in accordance with the preferred embodiment of the present invention.

A manufacturer device placement module 88 allows the manufacturer to view the location of the at least one implant device 16 in the patient's body as shown in FIG. 7. The physician can select the option "Patient Body" as shown in FIG. 6 to view the position of the implant device 16 in the patient's body. As shown in FIG. 7, an implant device icon 266 is positioned on a standard image 264 of the patient's body by the physician during a medical procedure to portray the location of the device 16 implanted in the patient's body as it relates to the procedure record shown in FIG. 6. As shown in FIG. 7, the manufacturer can view additional details including name of the implant device, serial number, the device lot number, and work type. The physician, the hospital and the patient can also view the implant device's location in the patient's body.

Figure 8:
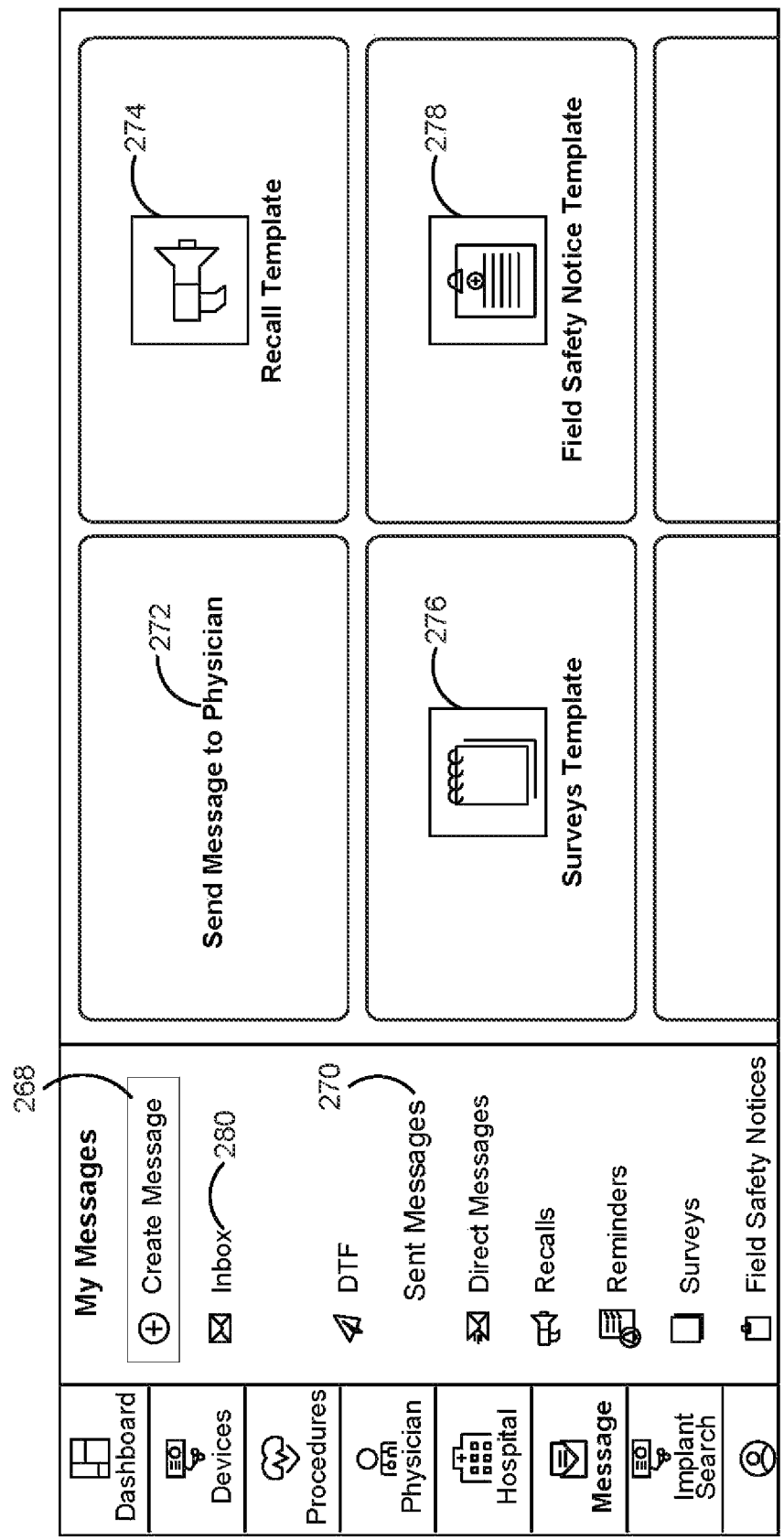
FIG. 8 illustrates a screenshot showing message templates for creating various types of messages in accordance with the preferred embodiment of the present invention.

A manufacturer outgoing message module 76 as shown in FIG. 2, manages communication and outgoing messages from the manufacturer. The manufacturer outgoing message module 76 displays a list of issued messages by the manufacturer. The manufacturer can view the issued messages sent by the manufacturer by selecting "Sent Messages" 270 as shown in FIG. 8. The manufacturer selects the option "Create Message" 268 to create a new message. There are several message templates for creating various types of messages such as a template for sending messages to the physician 272, a recall template 274, a survey template 276 and field safety notice template 278. The manufacturer incoming message module 74 as shown in FIG. 2 is configured to manage incoming messages from the physician and the hospital. The manufacturer can read the incoming messages by opening the "Inbox" 280 folder as shown in FIG. 8.

Figure 9:
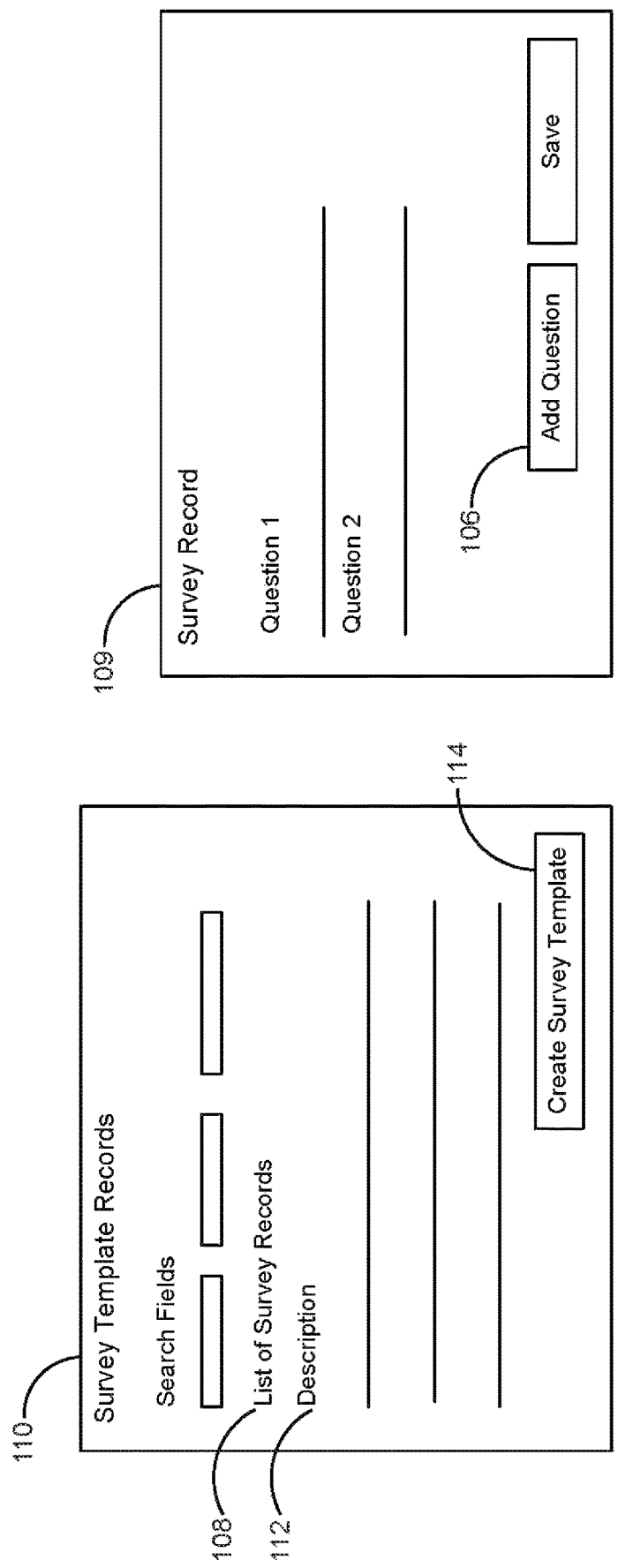
FIG. 9A illustrates a list of survey template records to perform a survey utilizing a survey management module in the implant manufacturer access unit in accordance with the preferred embodiment of the present invention.
FIG. 9B illustrates a survey record selected from the list of survey template records shown in FIG. 9A in accordance with the preferred embodiment of the present invention.

A survey management module 104 in the implant manufacturer access unit 34 shown in FIG. 2 performs at least one implant device survey. As shown in FIG. 9A, a survey template record 110 includes a group of searchable fields to enter search criteria into which a list of survey records 108 is displayed. The survey record list 108 includes survey description 112. When each entry in the survey description 112 is clicked, a detailed view of a survey record 109 is displayed as shown in FIG. 9B. Here, survey questions are captured as individual records. The user can add survey questions with answer fields by clicking "Add Question" 106 as shown in FIG. 9B. When the button "Create survey template" 114 as shown in FIG. 9A is clicked, a new blank device record for creating a new survey record is displayed. A survey result handling module 116 reviews survey responses from the at least one implant device survey.

A company information update module 82 in the implant manufacturer access unit 34 updates information associated with the implant manufacturer or a company. The company information update module 82 includes different methods to identify and save a list of all implant devices. The company information update module 82 enables the user to provide additional details, if any.

The implant manufacturer access unit 34 provides instructions for use (IFU) restrictions and requirements 56, the recall notices 236 and device information 61 to the at least one of the implant device 64 selected by the user.

Figure 10:
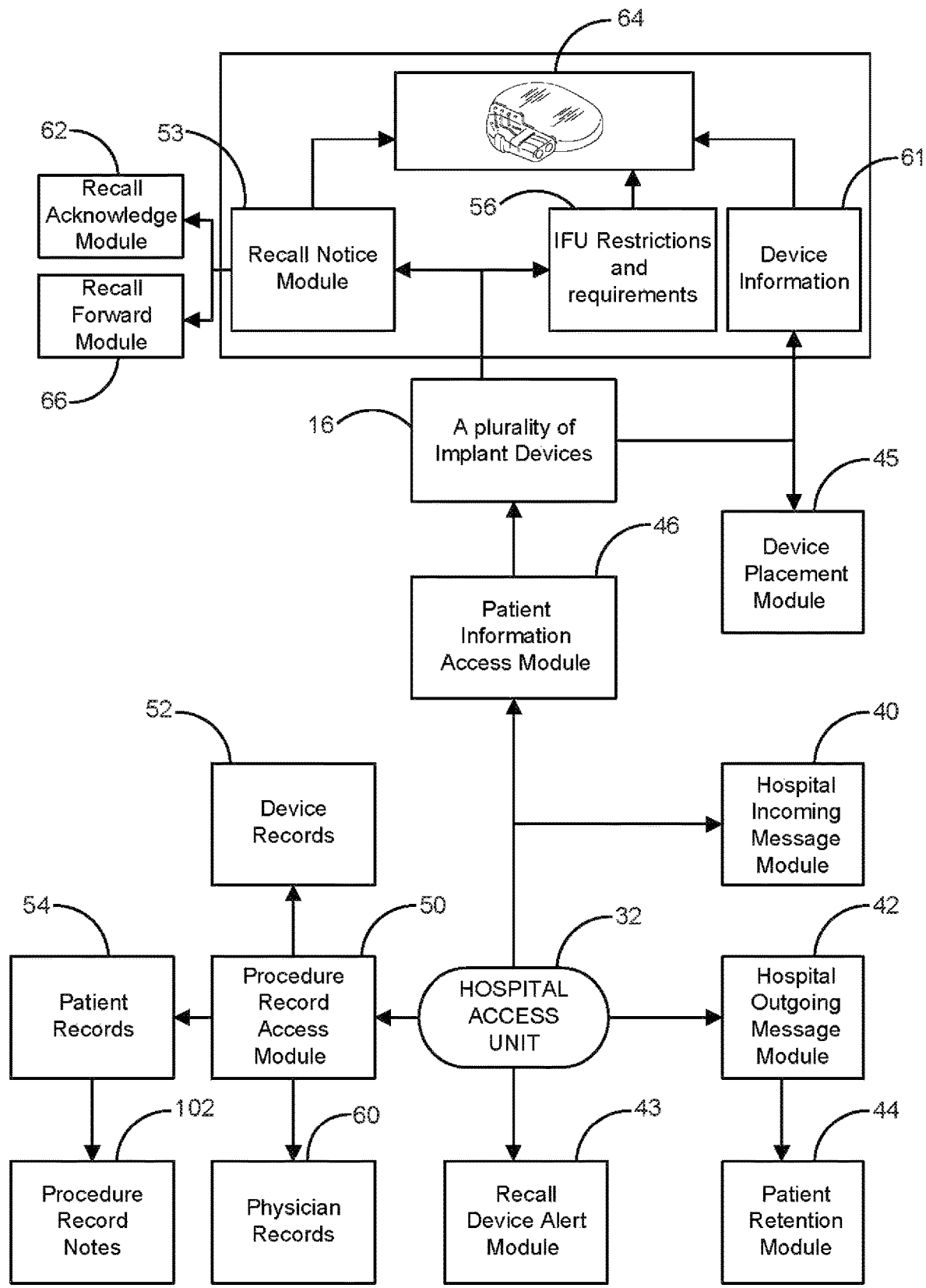
FIG. 10 illustrates a block diagram of a hospital access unit of the medical implant device tracking system in accordance with the preferred embodiment of the present invention.

FIG. 10 shows the hospital access unit 32. The hospital access unit 32 includes a hospital recall notice module 53 that enables the hospital to receive the at least one of the plurality of recall notices 236 from the manufacturer. A hospital acknowledgement module 62 allows the hospital to send the acknowledge confirmation notice to the manufacturer. Further, a hospital recall forward module 66 forwards the at least one of the plurality of recall notices 236 to the patient. The implant device tracking application automatically captures a list of recall-status of the patient having the recalled implant device and the device lot number 210 and automatically pushes the at least one of the plurality of recall notices 236 in the patient access unit 36.

A hospital device placement module 45 allows a hospital staff to view the location of the implant device 16 in the patient's body. The hospital staff may be an administrator or a nurse. A hospital recall device alert module 43 allows the hospital staff to receive the immediate notification of the recall status of the implant device 16 generated by the implant device tracking application at the time of the implant device scanning. The immediate notification prevents the implantation of the recalled implant device in the patient's body during a medical procedure thereby providing improved protection to the patients.

The hospital access unit 32 provides details such as instructions for use (IFU) restrictions and requirements 56, the recall notices 236 and device information 61 to a user selected implant device 64 as shown in FIG. 10.

Figure 11:
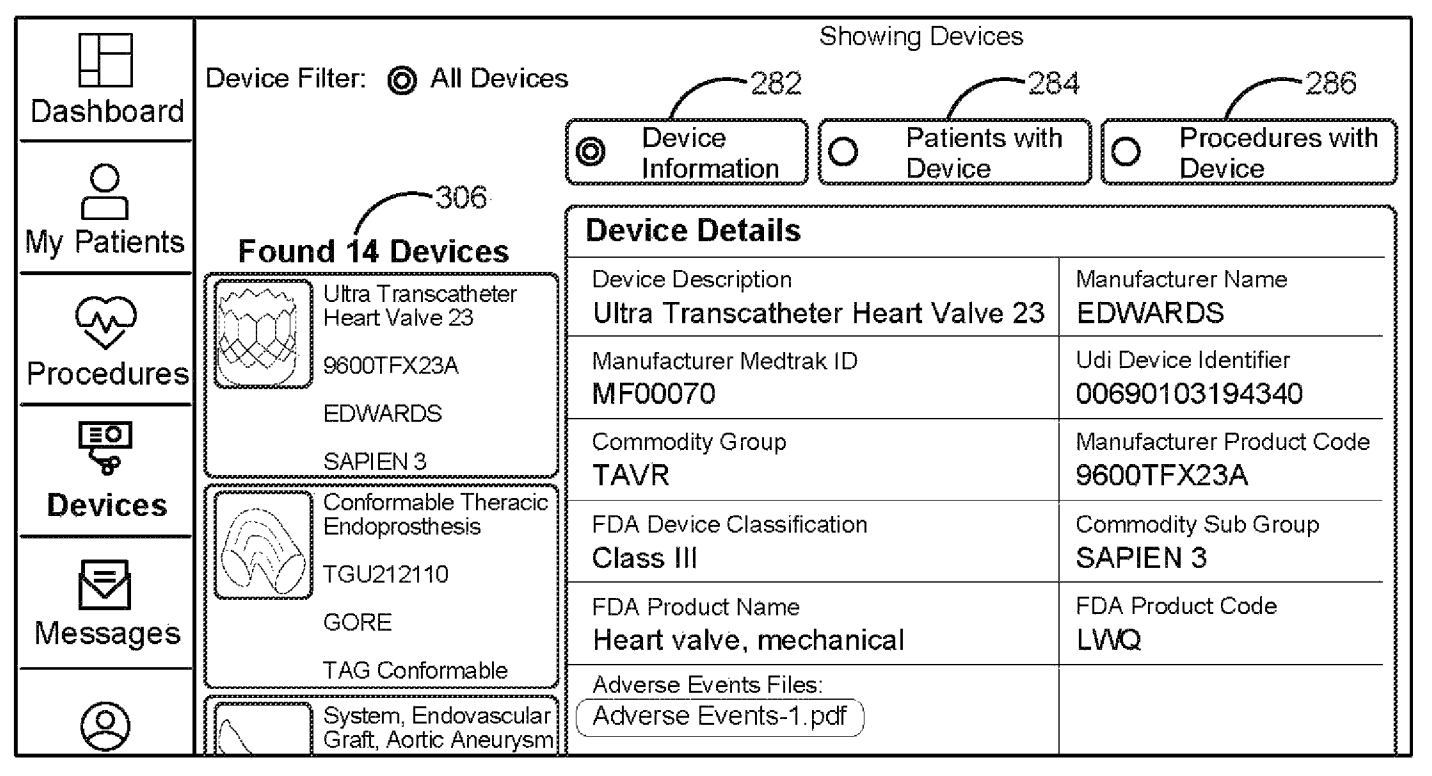

FIG. 11 shows implant device details viewed by the hospital staff through the communication device 12. The hospital staff can view details regarding Device Information 282, Patients with Device 284, and Procedure with Device 286. A detailed view of the implant device 16 can be viewed by selecting the record of each implant device. As shown in FIG. 11, the detailed view of each record of the implant device includes Device Description, Manufacturer Name, Manufacturer Tracking ID, Manufacturer Product Code, FDA Device Classification, FDA Product Name and FDA Product Code. The manufacture and the physician also can access and view the implant device details through the communication device 12.

A hospital incoming message module 40 is configured to manage incoming messages received by the hospital. The hospital inbound message may include device tracking forms, recall messages, field safety notices, or direct messages controlled by the implant device database. A hospital outgoing message module 42 manages an implant device communication section and the outgoing messages to the at least one communication device 12. The outgoing messages provide information regarding health checks or health advertisements to a patient retention module 44. A patient information access module 46 is configured to access patient information utilizing a searchable list of patients. The hospital access unit 32 further includes a procedure record access module 50 to access at least one procedure record of the patient utilizing a searchable list of procedure records and to create new procedure records. The searchable list of patients and the list of procedure records are stored in the implant device database. The list of procedure records includes but not limited to device records 52, patient records 54 and physician records 56. The patient records include procedure record notes 102.

Figure 12:
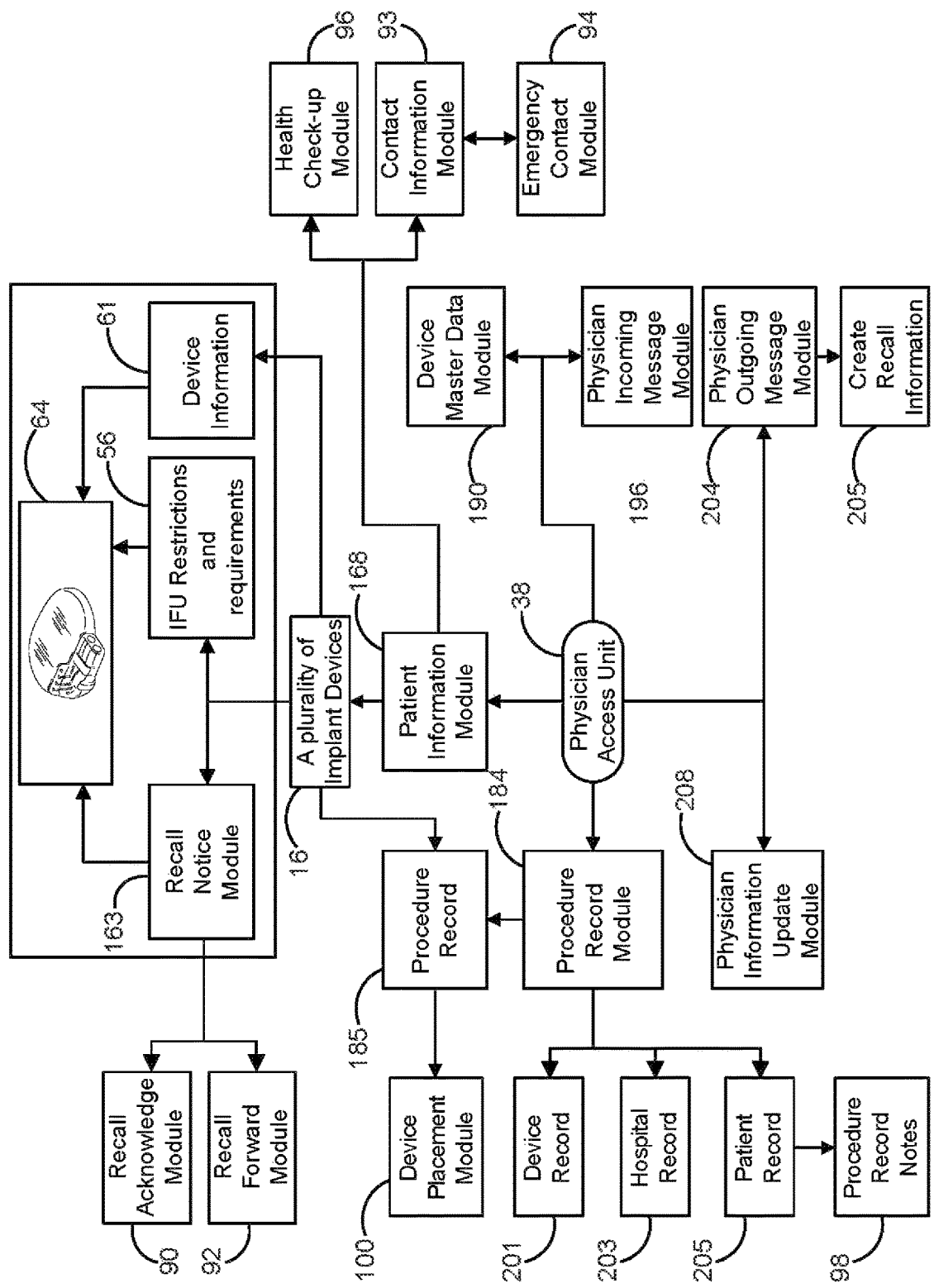
FIG. 12 illustrates a block diagram of a physician access unit of the medical implant device tracking system in accordance with the preferred embodiment of the present invention.
Figure 13:
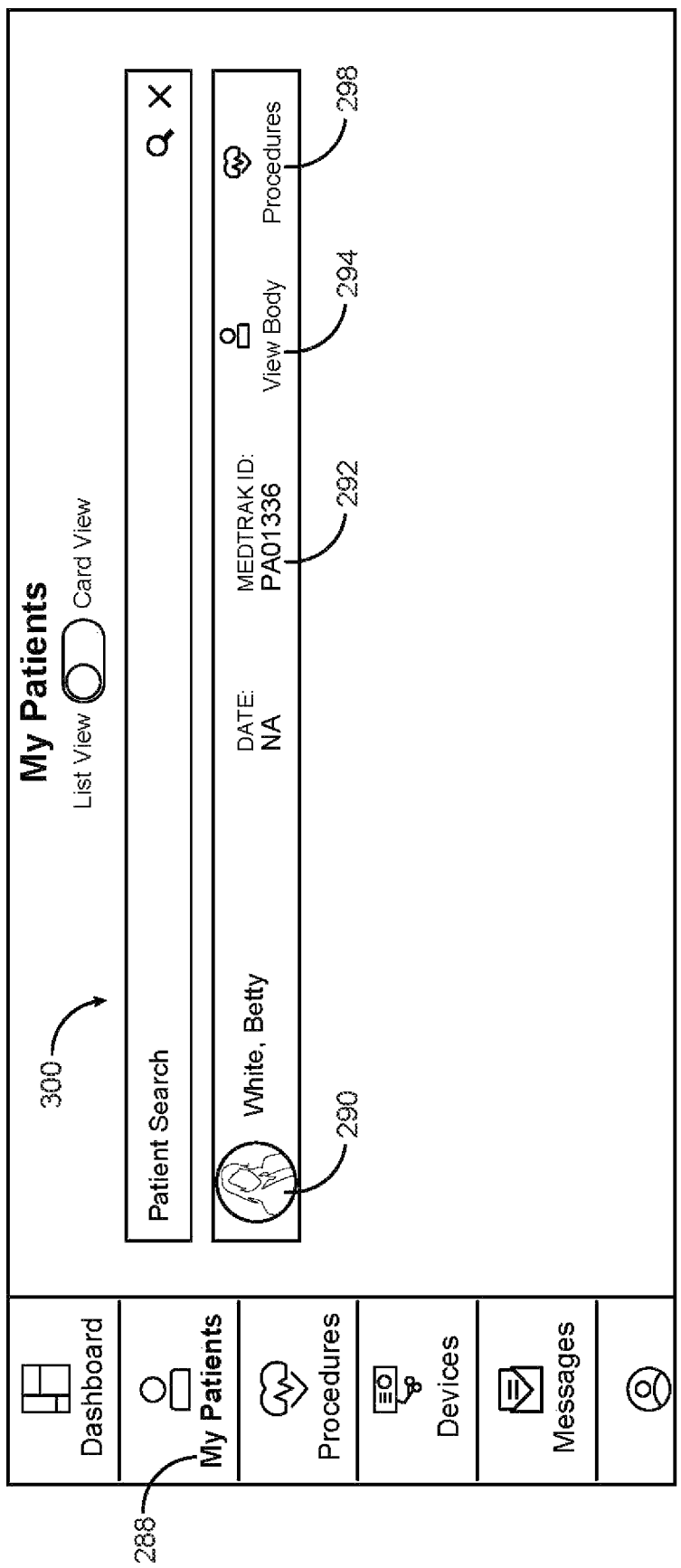
FIG. 13 illustrates a screenshot showing a list view of a patient record stored in an implant device database viewed by a physician in accordance with the preferred embodiment of the present invention.
Figure 14:
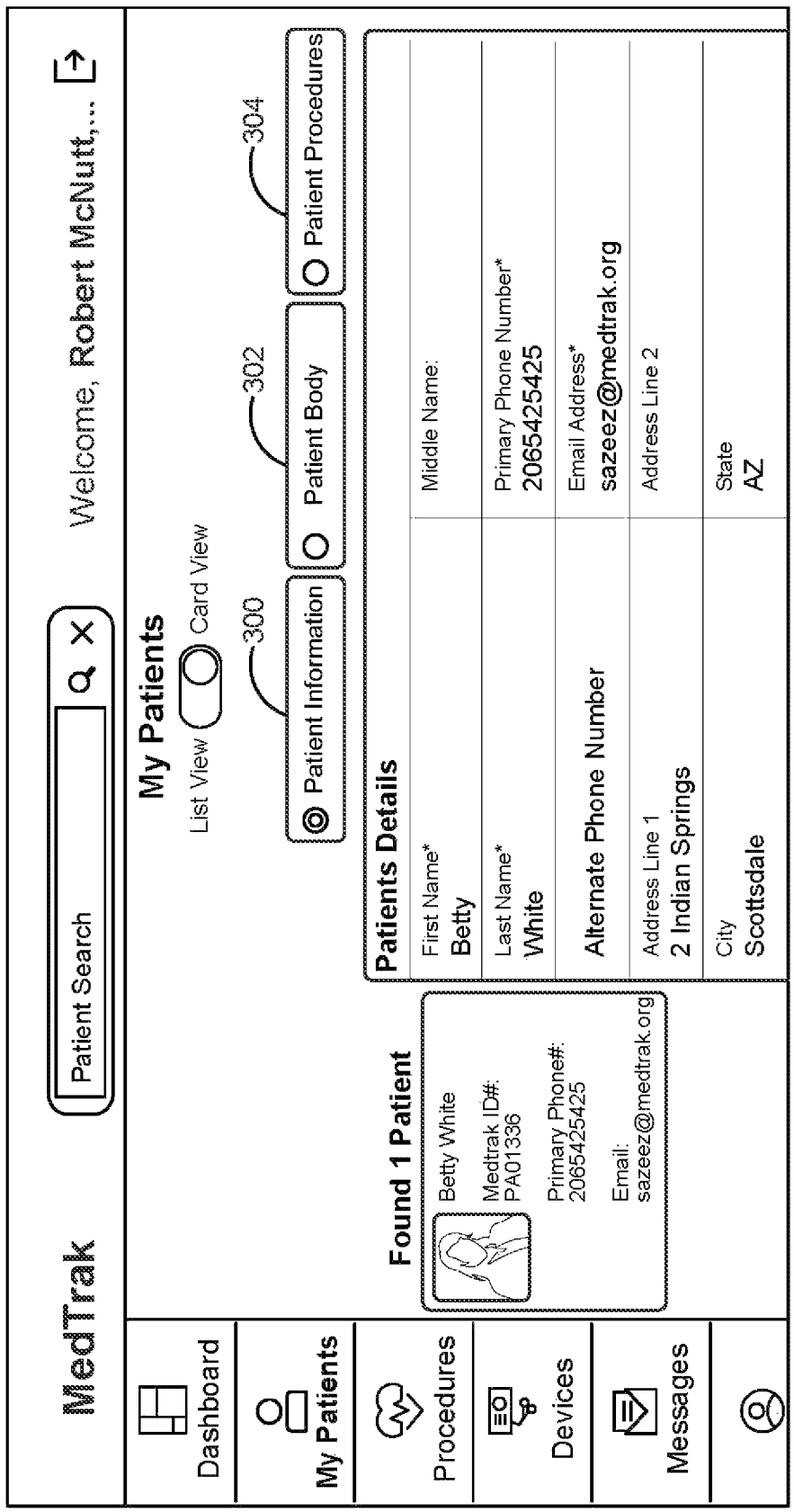
FIG. 14 shows a screenshot showing a card view of the patient record viewed by the physician shown in FIG. 13 in accordance with the preferred embodiment of the present invention.

The physician access unit 38 as shown in FIG. 12 is operatively coupled with the plurality of implant devices 16. The physician access unit 38 includes a patient information module 168 to view an existing patient record and to create a new patient record. The patient information module 168 enables to search patient records utilizing multiple search fields. FIG. 13 shows a list view of a patient record stored in the implant device database. The physician selects the option "My Patients" 288 from the menu bar and enters a keyword for searching and accessing patient information 300 including patient photo 290, device tracking ID 292, location of the implant device in the patient's body 294 and procedures 298. FIG. 14 shows a card view of the patient record displaying existing patient records. The physician can view details regarding various medical procedures by selecting the option "Patient Procedures"304. A physician device placement module 100 in the physician access unit 38 allows the physician to view the location of the implant device 16 in the patient's body. The physician can select the option "Patient Body" 302 as shown in FIG. 14 to view the position of the implant device 16 in the patient's body.

The physician access unit 38 includes a physician recall notice module 163 that enables the physician to receive the at least one of the plurality of recall notices 236 from the implant manufacturer. A physician acknowledgement module 90 allows the physician to send the acknowledge confirmation notice to the implant manufacturer. Further, a physician recall forward module 92 forwards the at least one of the plurality of recall notices 236 to the patient. The implant device tracking application automatically captures a list of recall-status of the patient having the recalled implant device and the device lot number 210 and automatically pushes the at least one of the plurality of recall notices in the patient access unit 38. A physician recall device alert module 183 allows the physician to receive the immediate notification of the recall status of the implant device 16 generated by the implant device tracking application at the time of the implant device scanning. The immediate notification prevents the implantation of the recalled implant device in the patient's body during a medical procedure.

Figure 15:
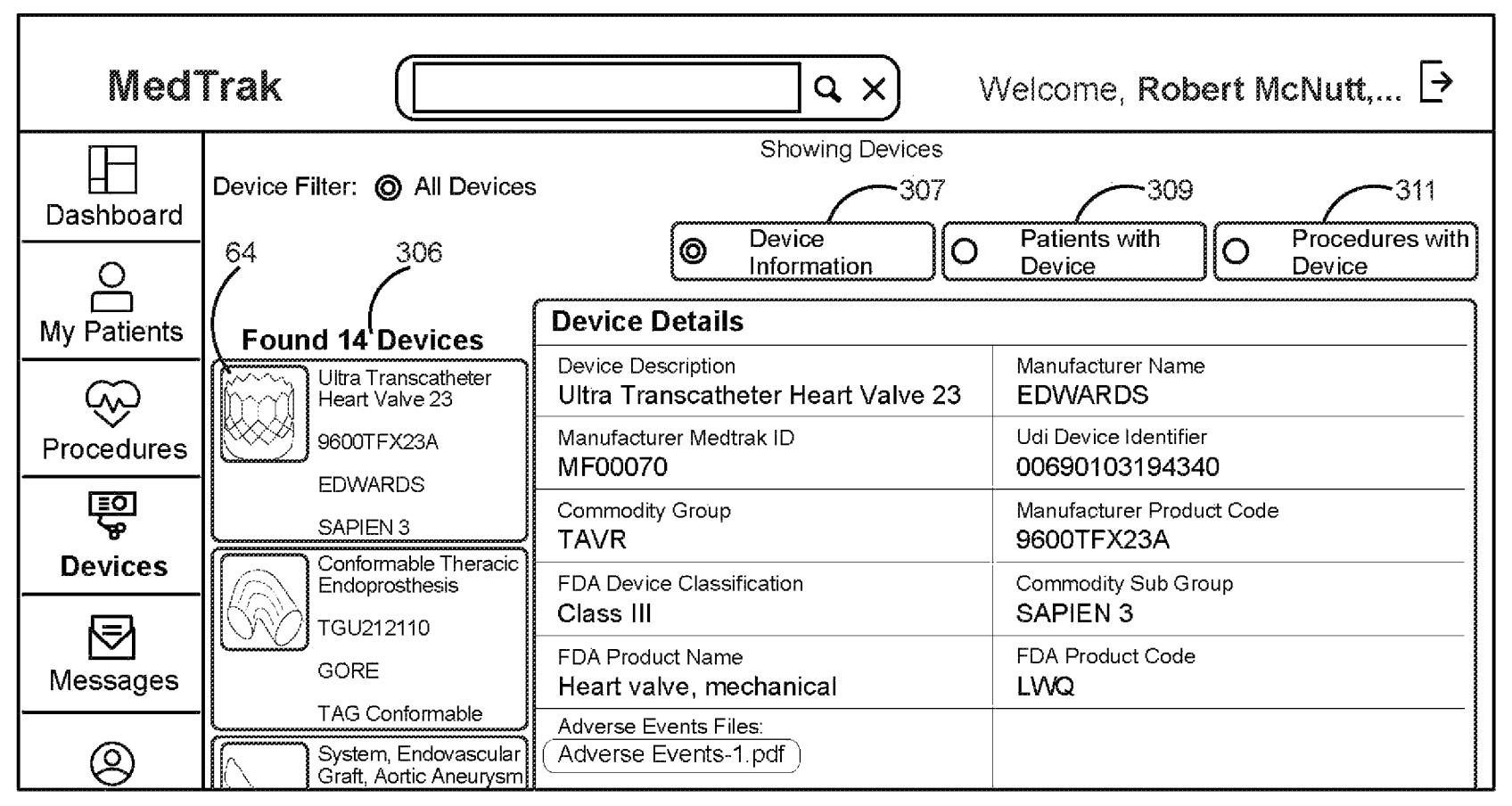

FIG. 15 shows implant device details viewed by the physician through the communication device 12. The physician searches for the implant device and filters the search result based on parameters "Device Information" 307, "Patients with Device" 309 and "Procedure with Device" 311. The physician can select an implant device 64 from the search result to view the detailed information regarding that device 64. The detailed view includes information such as Device Description, Manufacturer Name, Manufacturer Tracking ID, Manufacturer Product Code, FDA Device Classification, FDA Product Name and FDA Product Code. The manufacture and the hospital also can access the implant device details through the communication device 12.

The physician access unit 38 includes a procedure record module 184. The procedure record module 184 includes a procedure record 185, device record 201, a patient record 205 having procedure record notes 98, a hospital record 203 and a physician record 207. The procedure record module 184 is designed to view an existing procedure record and to create a new procedure record 185. A device master data module 190 is designed to access records of the implant devices 16. The device master data module 190 includes various methods to identify and save a list of all implant devices 16.

A physician contact information module 93 enables the physician to store contact information of the physician in the database unit. An emergency physician contact module 94 is designed to store emergency contact details of the physician in the implant device database. The physician access unit 38 further includes a physician health check-up module 96 to store a list of health checks and follow-up visit data in the implant device database.

Figure 16:
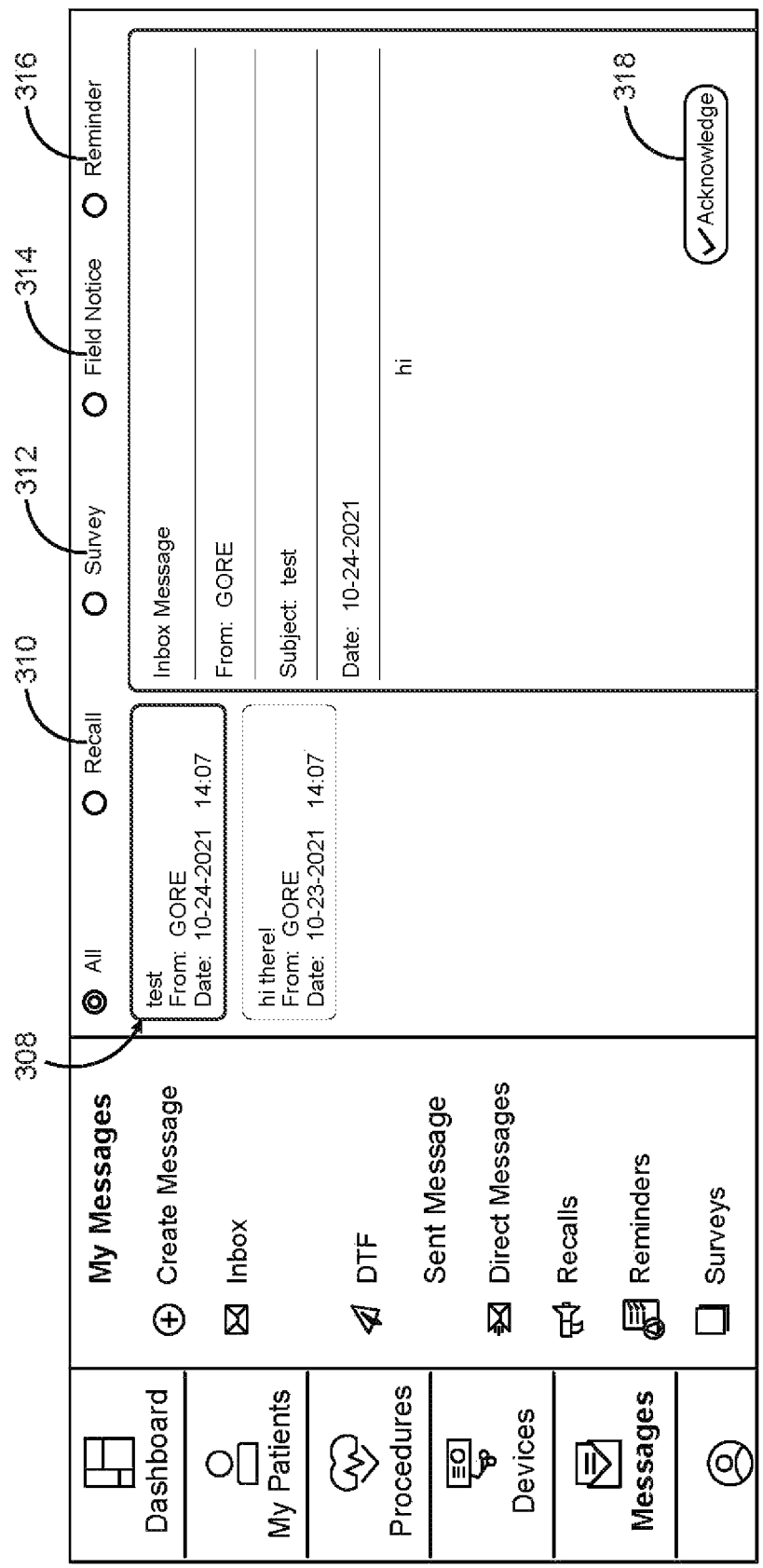
FIG. 16 illustrates a screenshot showing a list of physician incoming notices in accordance with the preferred embodiment of the present invention.
Figure 17:
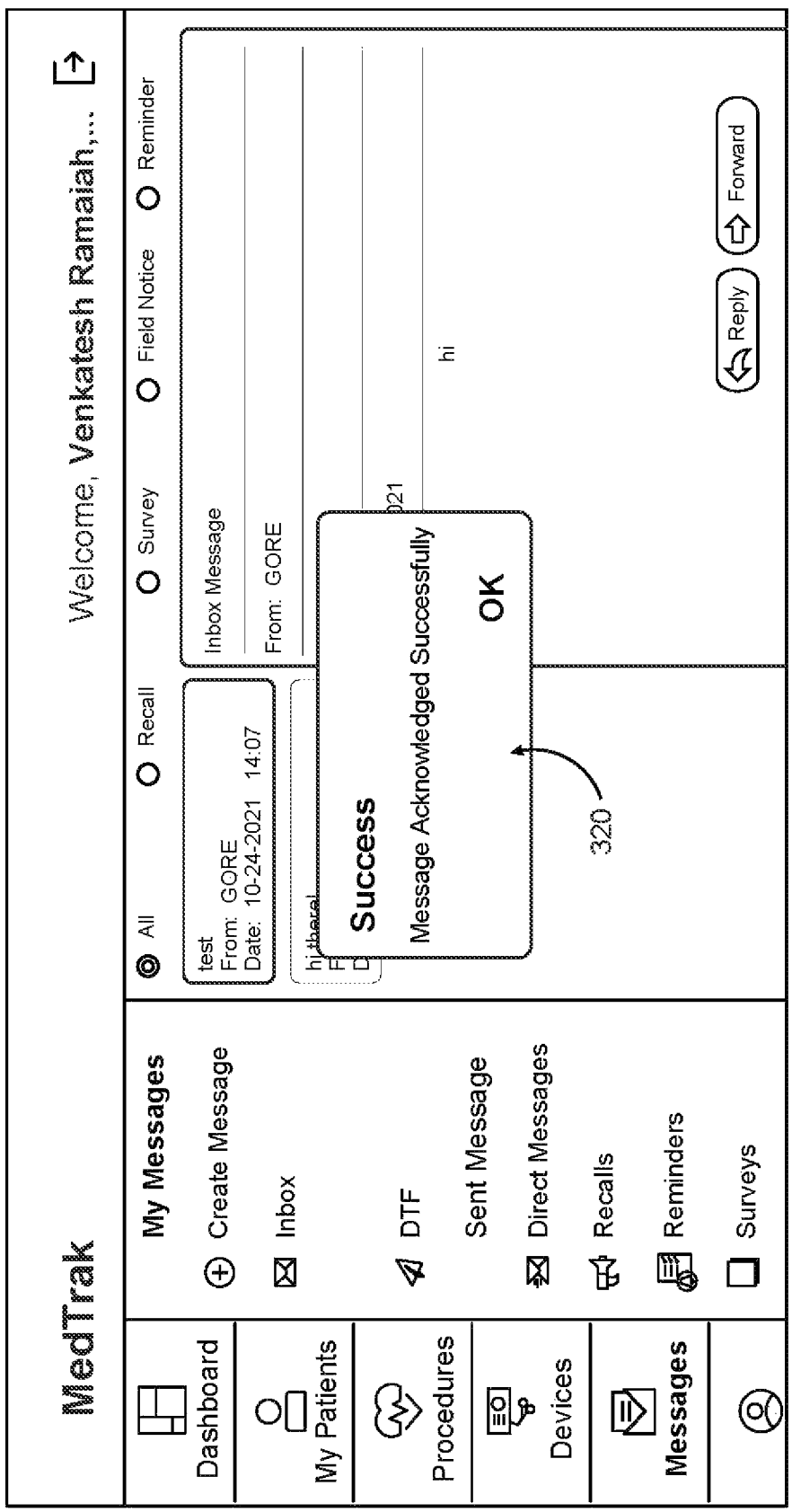
FIG. 17 illustrates a screenshot showing a pop-up window displaying an acknowledge message to the physician in accordance with the preferred embodiment of the present invention.
Figure 18:
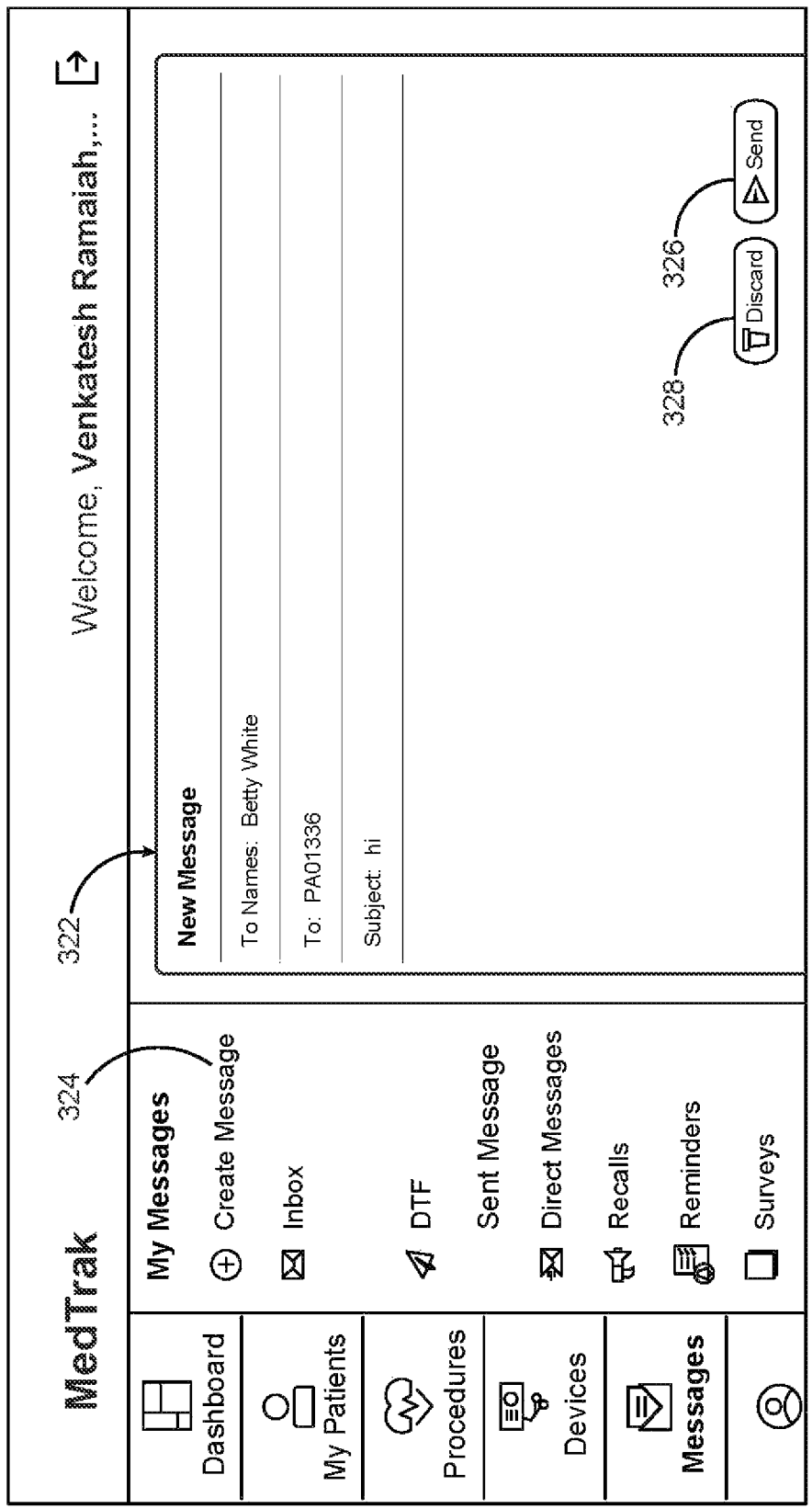
FIG. 18 illustrates a screenshot showing a new outgoing message created by the physician in accordance with the preferred embodiment of the present invention.

A physician incoming message module 196 is designed to create a list of physician incoming notices 308 as shown in FIG. 16. The list of physician incoming notices 308 notifies hospital appointment reminders and indicates the status of each physician incoming notice to the user such as whether the notice is acknowledged or not. The physician can filter the incoming messages based on parameters such as Recall 310, Survey 312, Field Notice 314, and Reminder 316. Each physician incoming notice 308 is designed to display message body, sender details and message subject. Upon reading the incoming message, the physician sends acknowledgement message by selecting the button "Acknowledge" 318. Thereafter, a pop-up window showing "Message Acknowledged Successfully" 320 is displayed to the physician as shown in FIG. 17. Further, the physician incoming notice module 196 notifies date/time at which the acknowledgement is captured. A physician outgoing message module 204 manages outgoing messages and the implant device communication section. The physician outgoing message module 204 creates a new outgoing message 322 and opens a new message template by selecting the option "Create Message" 324 as shown in FIG. 18. Each physician outgoing notice 198 displays message body, recipient details and message subject. By selecting "Send" 326 button the physician can send the message. If the Physician likes to discard the message, then he can press the "Discard" 328 button.

Figure 19:
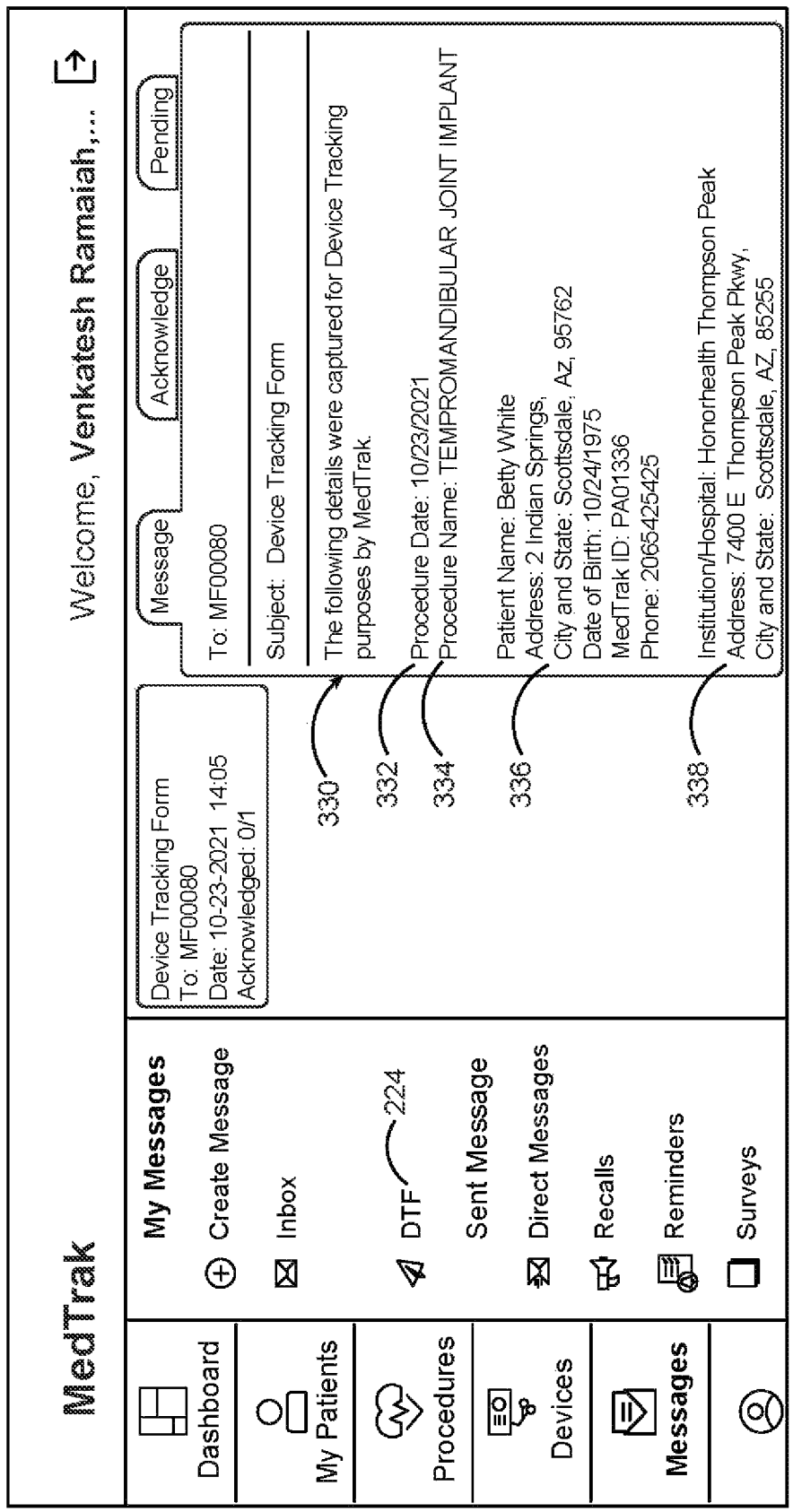
FIG. 19 shows a screenshot of a data tracking form (DTF) automatically generated by the implant device tracking system in accordance with the preferred embodiment of the present invention.

FIG. 19 shows a data tracking form (DTF) 330 that is automatically generated by the medical implant device tracking system 14 at the moment when the medical procedure is approved/closed by the physician. The DTF 330 is automatically routed to the associated implant device manufacturers of the procedure record. The physician creates the DTF 330 by selecting the option "DTF" 224 and sends the DTF 330 to the corresponding implant device manufactures. The DTF 330 includes the recipient address, message subject and message body. The DTF captures details including Procedure Date 332, Procedure Name 334, Patient details 336 and Hospital details 338.

Figure 20:
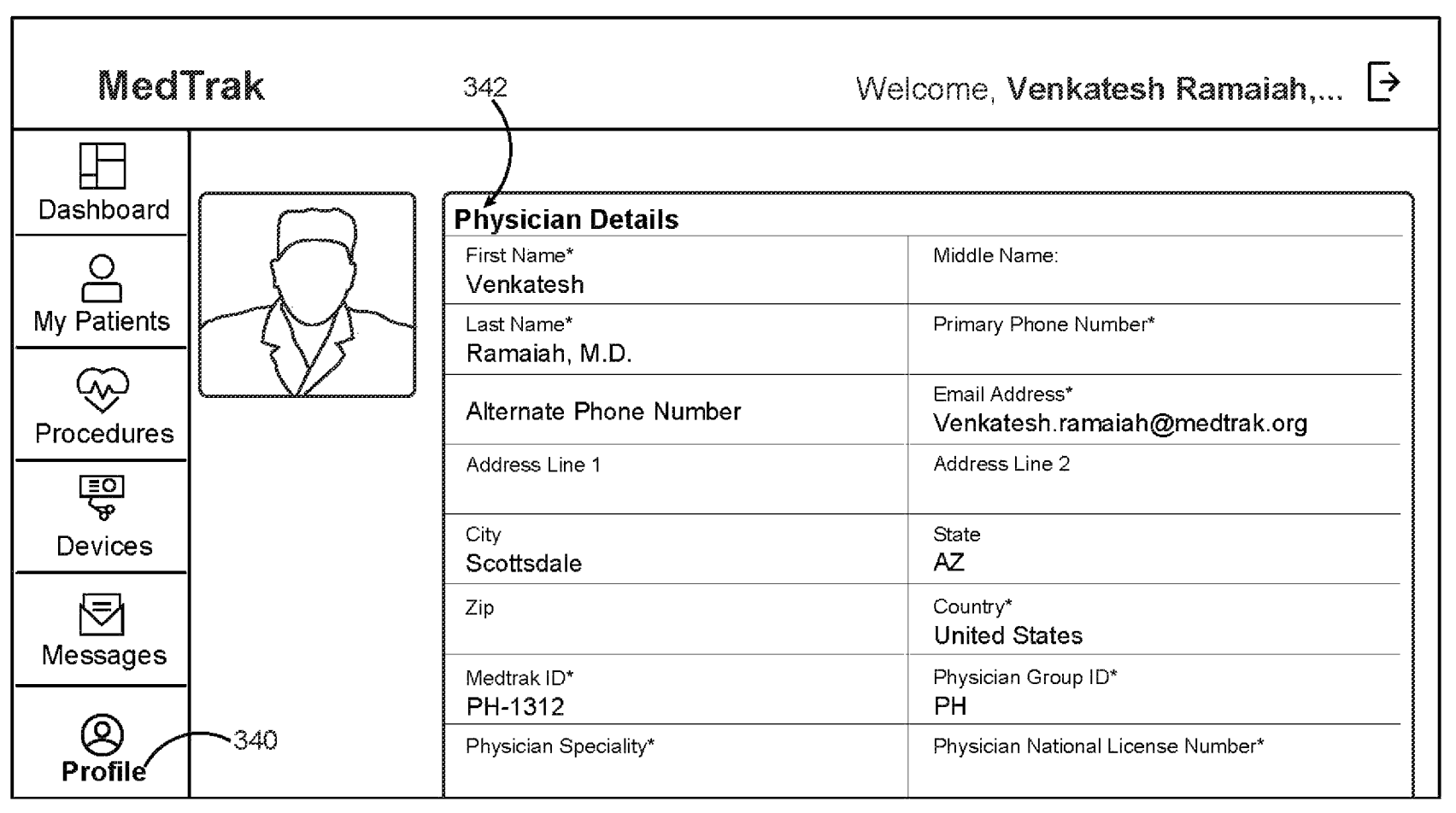

A physician information update module 208 updates contact information of the physician such as name, phone, E-mail, address, city, state/province, country, and zip/postal code. The entered details are updated in the implant device database. The physician can view the physician details 342 by selecting "Profile" as shown in FIG. 20. The physician access unit 38 provides IFU restrictions and requirements 56, the recall notices 236 and device information 61 to the user selected implant device 64 as shown in FIG. 12.

Figure 21:
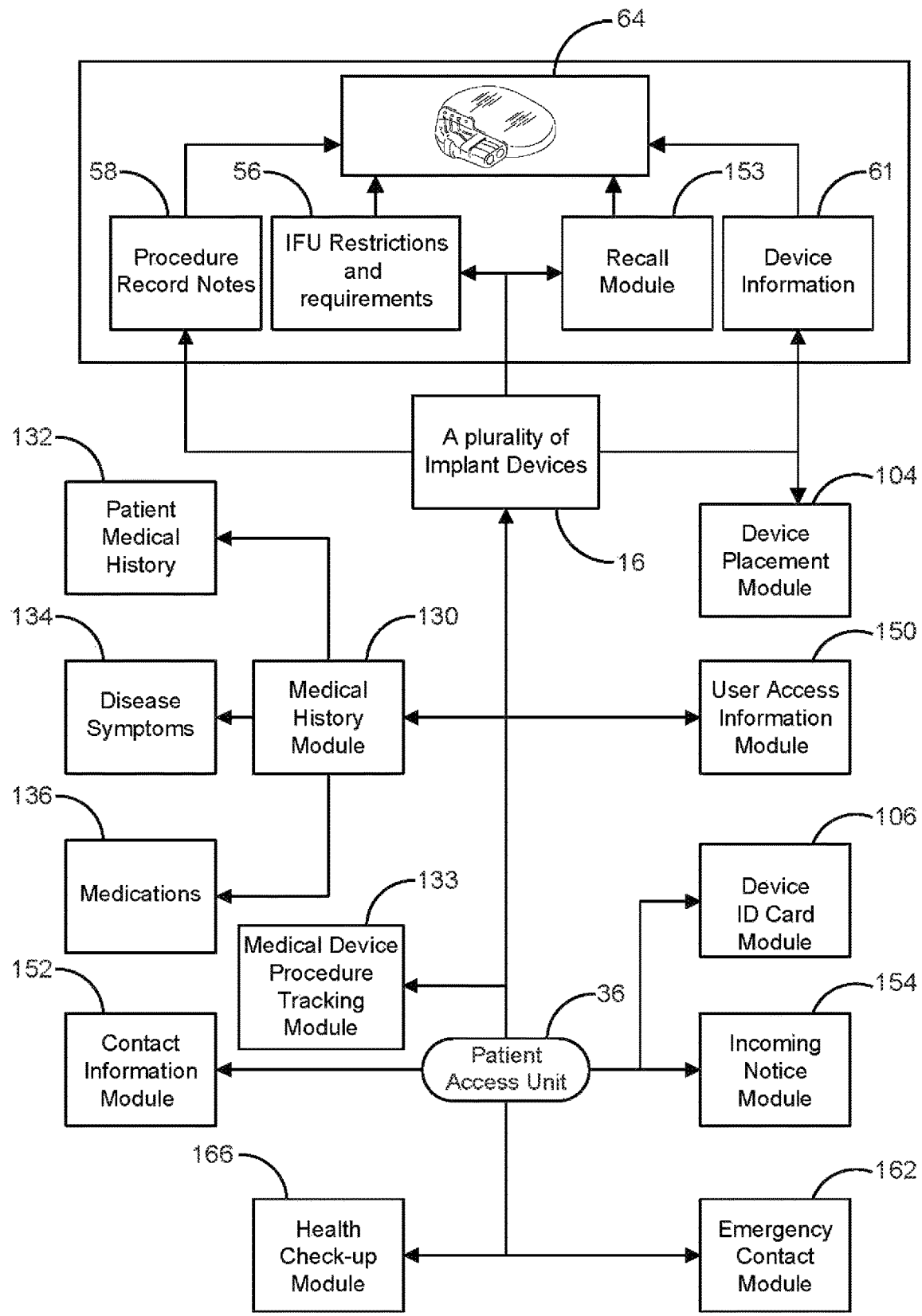
FIG. 21 illustrates a block diagram of a patient access unit of the medical implant device tracking system in accordance with the preferred embodiment of the present invention.

FIG. 21 illustrates the patient access unit 36. The patient access unit 36 includes a device ID card module 106 to provide an electronic wallet of a medical device ID card to the patient that allows the patient to store their critical medical device identification information in a password protected and traceable application. In the preferred embodiment, the medical device ID card is viewable and accessible to the patient at the moment a medical procedure is approved/completed by the physician. The medical device ID card stores the medical device identification information in an electronic format. Further, the device ID card module 106 allows the patient to access the medical device ID card from anywhere and at any time as desired utilizing the protected and traceable application. A patient recall module 153 enables the patient to receive the at least one of the plurality of recall notices 236 forwarded by the physician and the hospital.

The process for creating and managing the recall notices 236 in the preferred embodiment can be summarized as: the manufacturer selects the at least one implant device 16 and the device lot number 210. Then, the manufacturer creates the recall notice 236 and attaches a recall date to the recall notice 236. The device lot number 210 for all procedures with that implant device 16 as well as shelved products is searched in the implant device database connected to the hospital access unit 32, the physician access unit 38, or the implant manufacturer access unit 34. The recall notices 236 are automatically routed to the corresponding physician and the hospital utilizing the secured notification process of the medical implant device tracking system 14. The physician and the hospital receives the recall notice 236 and sends an acknowledge notice to the manufacturer. The manufacturer receives confirmation of that acknowledge notice in the sent recall acknowledge list. The hospital or the physician forwards the recall notice 236 to the patient. The implant device tracking application automatically captures all patients with the recalled device and the device lot number 210 and the recall notice 236 is automatically pushed to the patient access unit 36.

Figure 22:
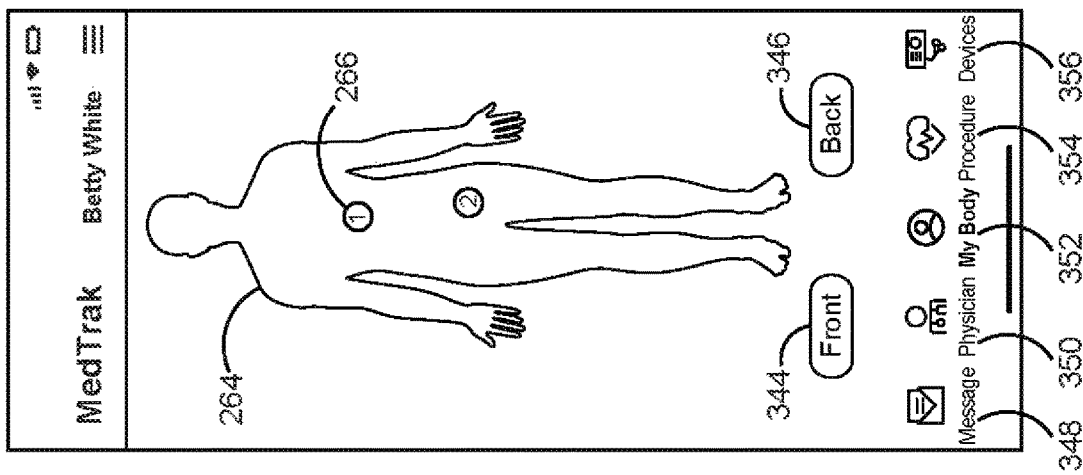
FIG. 22 illustrates the location of the implant device positioned in the patient's body viewed by the patient through a mobile phone in accordance with the preferred embodiment of the present invention.

A patient device placement module 104 in the patient access unit 36 allows the patient to view the location of the at least one implant device 16 in the patient's body. FIG. 22 shows the location of the implant device 16 positioned in the patient's body viewed by the patient through the mobile phone. Here, the implant device icon 266 is positioned on the standard image 264 of the patient's body. The patient can view the front portion of the body image by selecting the button "Front" 344 and the back portion by selecting the button "Back" 346. The patient can view additional details by selecting Messages 348, Physician 350, My body 352, Procedure 354 and Devices 356 from the menu bar.

A medical history module 130 stores information regarding patient medical history 358, medications 364 and disease symptoms 370 in the database unit 30 as shown in FIGS. 23A-23C. The medical history form 358 includes a list of medical history details 360. Each entry in this list 360 represents the medical history form 358 filled by the patient. The list of medical history details 360 includes date and patient name. A button "New medical history form" 362 is clicked to open a new editable medical history form for the patient to fill out. As shown in FIG. 23B, the medication details form 364 includes medicine prescribed date, patient details, drug name, dosage frequency of drug use and details of discontinued drugs. As shown in FIG. 23B, the discontinued drugs are clearly marked by a line 366. A disease symptom information form 370 as shown in FIG. 23C includes a list of symptom entries and each entry in this list represents a previously filled symptom form completed by the patient. As shown in FIG. 23C, the symptom form 370 includes date and patient name. A button "New symptom data form" 368 is clicked to open a new editable symptom data form for the patient to fill out.

Figure 25:
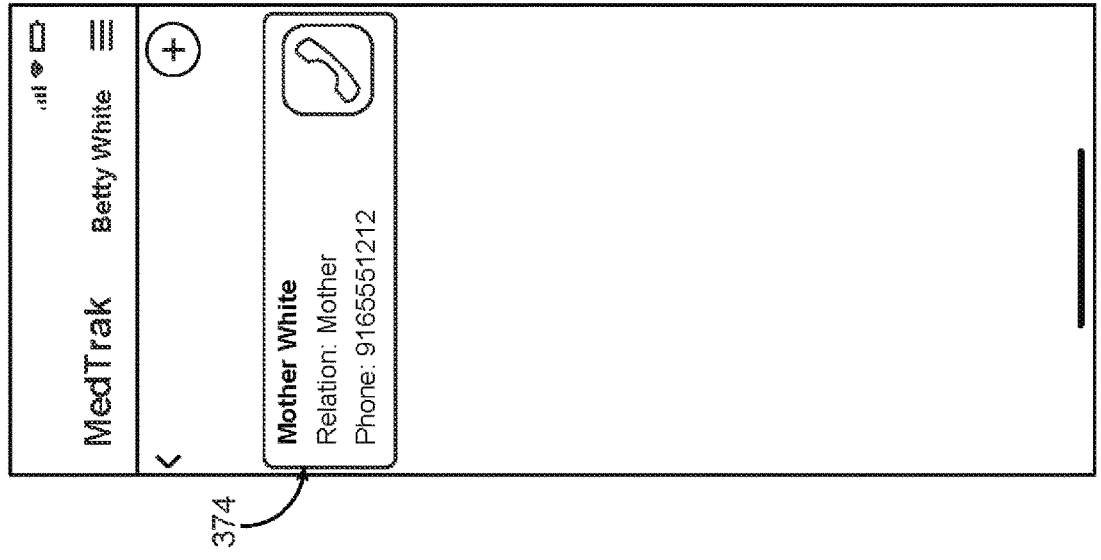
FIG. 25 illustrates a screenshot of an alternate contact details of the patient in accordance with the preferred embodiment of the present invention.
Figure 24:
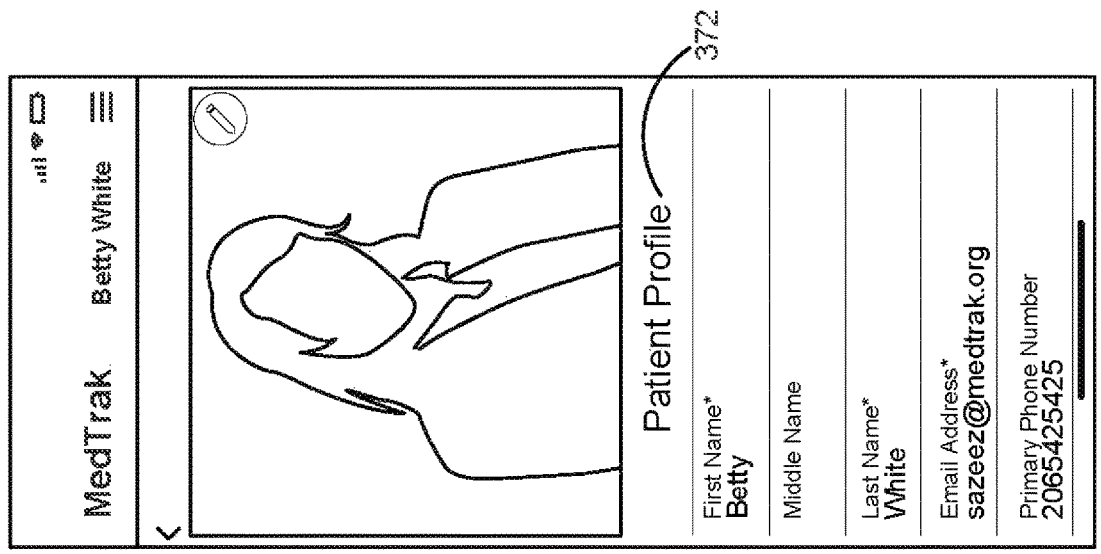
FIG. 24 illustrates a screenshot of a patient profile in accordance with the preferred embodiment of the present invention.

A medical device procedure tracking module 133 in the patient access unit 36 enables the patients to access their device information, recall information, procedure notes procedure images and the location of the implant device 16 on the image 264 of the patient body. A patient contact information module 152 enables the system 14 to store contact information of patients in the database unit 30. This module 152 enables to update current patient contact information such as name, phone, E-mail, address, city, state/province, country, and zip/postal code. FIG. 24 shows a patient profile 372 that displays patient name and contact details. The contact information module 152 enables the patient to provide additional details other than the profile details 372 shown in FIG. 24. FIG. 25 shows alternate contact details 374 of the patient. The alternate contact details 374 can be utilized in case of emergency thereby ensuring the safety of the patients.

Figure 26B:
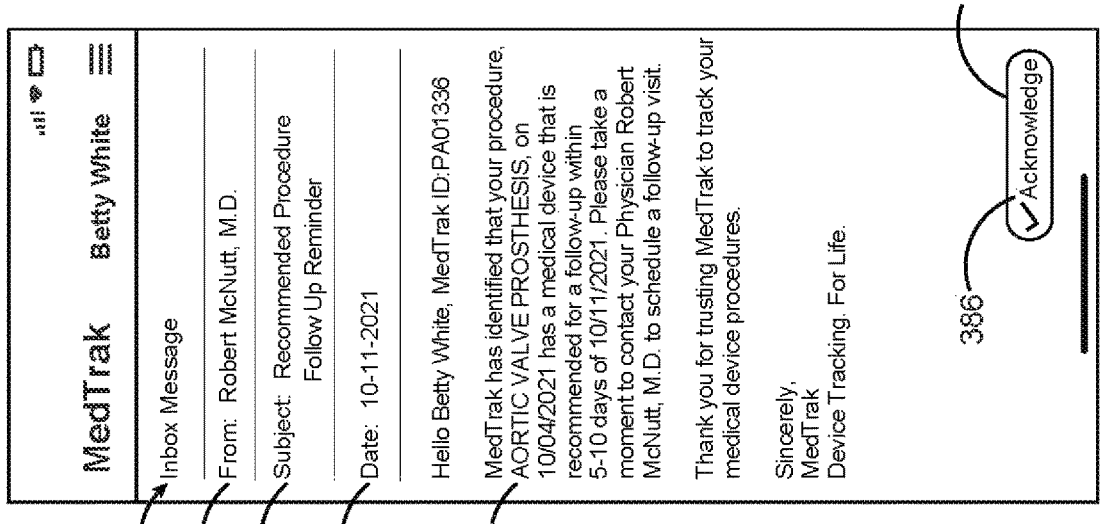
FIG. 26B illustrates a screenshot of a detailed view of an incoming procedure notice selected from the list of incoming procedure follow up notices shown in FIG. 26A in accordance with the preferred embodiment of the present invention.
Figure 26A:
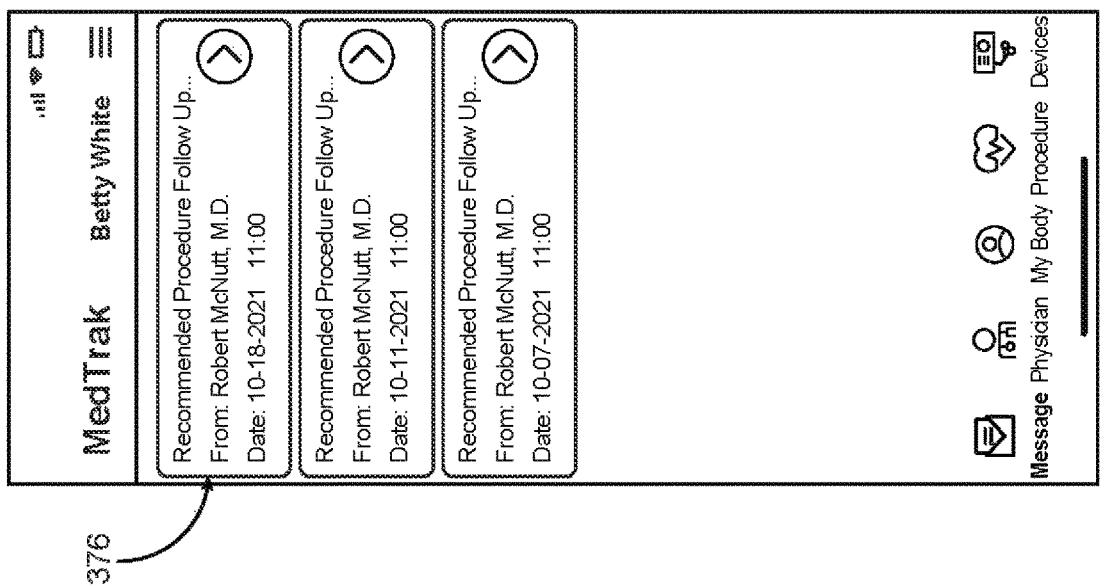
FIG. 26A illustrates a screenshot of a list of incoming procedure follow up notices sent to the patient by the physician in accordance with the preferred embodiment of the present invention.

A patient incoming notice module 154 notifies of hospital appointment reminders and the status of each notice to the patient such as whether the notice is acknowledged or not. Further, the incoming notice module 154 notifies date/time at which the acknowledgement was captured. The type of messages includes recall notice, field safety, etc. As shown in FIG. 26A, a list of incoming procedure follow-up notices 376 is sent to the patient by the physician. By clicking each entry in the list of incoming notices 376, a detailed view of that particular incoming message 381 is displayed as shown in FIG. 26B. The incoming message 381 includes message subject 378, message body 384, date 380 and message sender 382. The incoming notices 376 notify the patient that the messages are waiting to be viewed and indicate the number of messages which are not yet viewed. Further, the patient can acknowledge the incoming messages by selecting the button "Acknowledge" 586.

An emergency contact module 162 stores emergency contact details of the patient in the database unit 30. The patient access unit 36 includes a health checks and follow-up module 166 to store a list of health checks and follow-up visit data in the database unit 30. Initial procedure record of the patient supplies a first date. Following dates and notes will come from the log entries from the physician designated as "Follow-Up". The health checks and follow-up visit data provide an appointment history of the patient for providing to a new doctor.

The patient access unit 36 provides procedure record notes 58, IFU restrictions and requirements 56, the recall notices 236 and device information 61 to the user selected implant device 64 as shown in FIG. 21.

Figure 27:
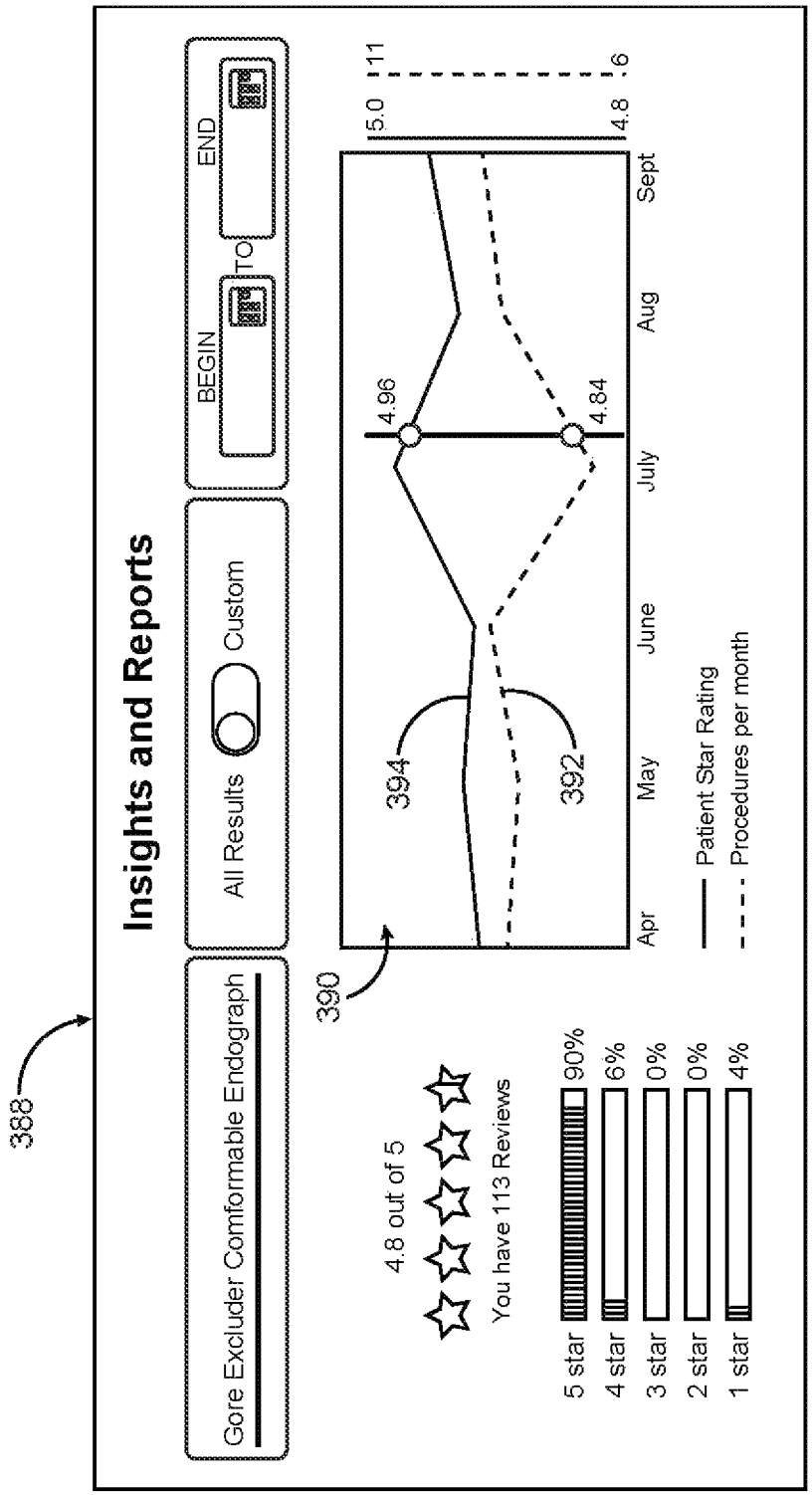
FIG. 27 illustrates a patient feedback report generated by the medical implant device tracking system in accordance with the preferred embodiment of the present invention.

FIG. 27 shows a patient feedback report 388 generated by the medical implant device tracking system 14. The feedback report 388 is designed to collect feedback directly from patients about their implant devices 16, physician and other facilities. The patient can provide a star rating for their devices and hospitals. Further, a graphical representation 390 of a patient star rating 394 and procedure per month 392 is also included in this feedback report 388.

Figure 28:
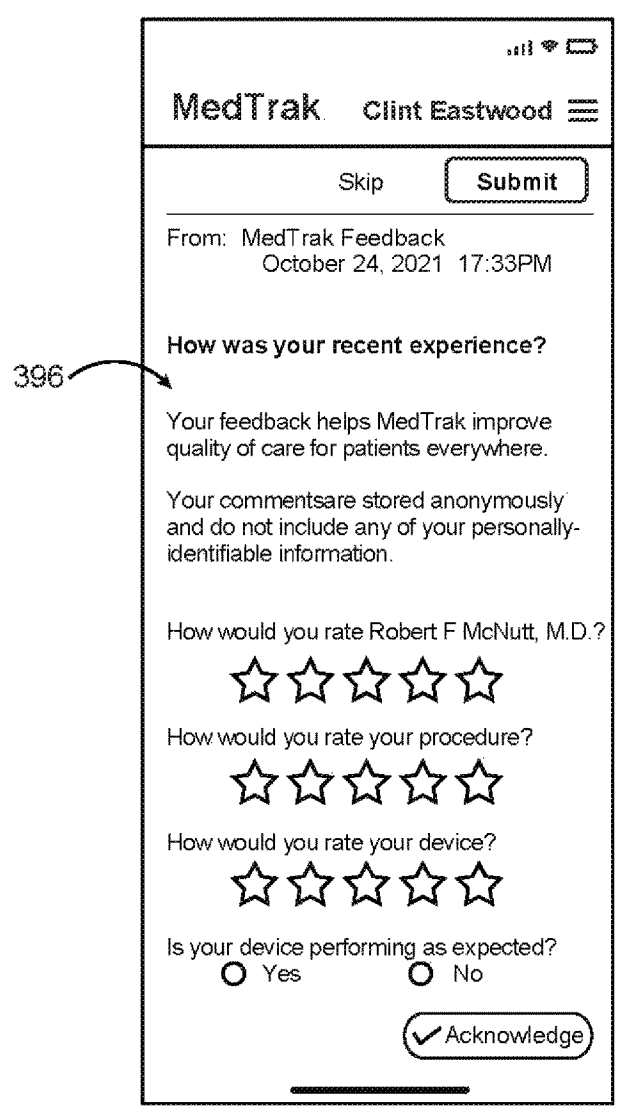
Figure 29:
FIG. 29 illustrates revision for tracking recalls and device locations utilizing a recalled device tracking module in the implant manufacturer unit of the medical implant device tracking system in accordance with the preferred embodiment of the present invention.

FIG. 28 shows a feedback form 396 provided to the patients to enter their recent experience with the physician, medical procedure, and the implant device 16. FIG. 29 shows revision for tracking recalls and device locations. The recalled device tracking module 75 as shown in FIG. 2 enables the implant manufacturer to view the location and status of the implant devices 16 related to a device recall utilizing the device lot number. For example, as shown in FIG. 29, when a device Lot "7909-004" is entered for a device search, the manufacturer receives a message "Devices from this Lot were recalled on Aug. 28, 2021". In this way, the system 14 informs the status of the implant device 16 to the manufacturer after a device recall. Further, the device tracking module 75 displays unassigned inventory as shown in FIG. 29. This is a unique feature of the system 14 that displays whether a message has been sent, has acknowledged, has a pending response, and enables the implant manufacturer to view the most critical device recalls requiring attention.

One form of the system 10 may communicate with the implanted patient via a program utilized on a computer, a mobile device, or via the web as software as a service (SaaS). A mobile device may be a wireless mobile device or any type of portable computer device, including a cellular telephone, a Personal Digital Assistant (PDA), smartphone, etc. Most, if not all, of these mobile devices include a built-in camera that can be controlled by software applications. In some embodiments, mobile devices comprise a camera, a processor, a graphical user interface (GUI), and memory. In embodiments, the memory is operatively coupled to the processor and stores program instructions that when executed by the processor, causes the processor to receive an image from the camera. Said image may be displayed on the GUI. The GUI may also receive descriptive data for the image and store the descriptive data and image as a listing. Generally, said listing may be transmitted wirelessly to a host server. The system may not only keep track of the implanted device and attention that may require in relation thereto but may also allow patients to monitor what medicines they are on and to keep track of medical appointments. The application may also include the option to communicate with a physician, hospital, device manufacture, insurance company etc.

In one embodiment, the system further comprises a procedure record access module that records the implanted device details, including serial numbers and lot numbers; a procedure record that includes a procedure log entry allowing the procedure team to document details about the procedure and enables storing of Electronic Images in several image formats and can be accessible using the industry standard Digital Imaging and Communications in Medicine (DICOM) format; a procedure record access module accessible for physician, hospital, manufacturer users to enter procedure data on behalf of the physician during the procedure; a procedure record must be reviewed by physician of record and approved by physician of record; a procedure record log entry must be reviewed by the physician of record and can be made viewable and accessible to patients after procedure record is approved; and wherein a procedure record log entry has settings that will automatically send procedure notifications to device manufacturer to immediately report device complications or other such FDA mandated device reporting requirements.

The system my further comprise a procedure record access module that records the implanted device details, including serial numbers and lot numbers; a procedure record that includes a procedure log entry allowing the procedure team to document details about the procedure and enables storing of Electronic Images in several image formats and can be accessible using the industry standard Digital Imaging and Communications in Medicine (DICOM) format used in Electronic Health Records (EHR); a procedure record access module accessible for physician, hospital, manufacturer users to enter procedure data on behalf of the physician during the procedure; wherein a procedure record must be reviewed by physician of record and approved by physician of record; wherein a procedure record log entry must be reviewed by the physician of record and can be made viewable and accessible to patients after procedure record is approved; and wherein a procedure record log entry has settings that will automatically send procedure notifications to device manufacturer to immediately report device complications or other such FDA mandated device reporting requirements.

The system my further comprise a procedure record module to review and approve and existing procedure record; wherein a procedure record access module records the implanted device details, including serial numbers and lot numbers; a procedure record that includes a procedure log entry allowing the procedure team to document details about the procedure and enables storing of Electronic Images in several image formats and can be accessible using the industry standard Digital Imaging and Communications in Medicine (DICOM) format used in Electronic Health Records (EHR); a procedure record access module accessible for physician, hospital, manufacturer users to enter procedure data on behalf of the physician during the procedure; wherein a procedure record must be reviewed by physician of record and approved by physician of record; wherein a procedure record log entry must be reviewed by the physician of record and can be made viewable and accessible to patients after procedure record is approved;

wherein a procedure record log entry has settings that will automatically send procedure notifications through the at least on communication module to device manufacturer to immediately report device complications or other such FDA mandated device reporting requirements; and wherein a procedure record access module that automatically generates procedure notifications, as deemed mandatory, to the appropriate users, such as physician, hospital and manufacturer; and wherein a procedure record automatically generates a device tracking form that attaches to the procedure record and automatically generates a message of notification through the at least on communication module to the appropriate user, such as hospital, physician, manufacturer.

In yet another embodiment (16), the system further comprises a procedure record access module that records the implanted device details, including serial numbers and lot numbers; wherein a procedure record that includes a procedure log entry allowing the procedure team to document details about the procedure and enables storing of Electronic Images in several image formats and can be accessible using the industry standard Digital Imaging and Communications in Medicine (DICOM) format; further comprising a procedure record access module accessible for physician, hospital, manufacturer users to enter procedure data on behalf of the physician during the procedure; wherein a procedure record must be reviewed by physician of record and approved by physician of record; wherein a procedure record log entry must be reviewed by the physician of record and can be made viewable and accessible to patients after procedure record is approved; wherein a procedure record log entry has settings that will automatically send procedure notifications to device manufacturer to immediately report device complications or other such FDA mandated device reporting requirements; wherein a procedure record log entry must be reviewed by the physician of record and can be made viewable and accessible to patients after procedure record is approved; wherein a procedure record log entry has settings that will automatically send procedure notifications through the at least on communication module to device manufacturer to immediately report device complications or other such FDA mandated device reporting requirements; wherein a procedure record access module that automatically generates procedure notifications, as deemed mandatory, to the appropriate MedTrak users, such as physician, hospital and manufacturer; and wherein a procedure record automatically generates a device tracking form that attaches to the procedure record and automatically generates a message of notification through the at least on communication module to the appropriate MedTrak user, such as hospital, physician, manufacturer.

In yet another embodiment (20) the system is capable of enabling a manufacturer to receive automated notifications of secondary procedures, device complications and device tracking details; enabling a manufacturer to create procedure records on behalf of physician; enabling manufacturer to view an inventory of implanted device procedures; enabling the patient to send an acknowledge confirmation to the physician and/or the hospital utilizing the patient acknowledge module; enabling all parties to retain acknowledgements for future use and reporting; enabling all parties to view participants acknowledge or pending acknowledgement; and enabling the manufacturer to view inventory of recall devices for administering retrieval of recall product.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention to not be limited by this detailed description, but by the claims and the equivalents to the claims appended hereto.

What is claimed is:

1. A system for identifying and tracking a plurality of implant devices, the system comprising:
   at least one communication device operatively coupled with at least one of the plurality of implant devices; and
   a medical implant device tracking system in communication with the at least one communication device and the plurality of implant devices via a network, the medical implant device tracking system including an implant tracking server residing on a central computer having a processor on which is installed an implant device tracking application and coupled with a memory unit integrated with a central database, the implant device tracking application enables the at least one communication device to scan a unique device identifier (UDI) of the at least one of the plurality of implant devices thereby recording a complete and accurate set of information about the at least one of the plurality of implant devices, the medical implant device tracking system comprising:
   a database unit configured to store and manage implant device information in an implant device database and logic to manage and route data to the at least one communication device;
   an implant manufacturer access unit including:
      a data collecting and reporting module to manage a plurality of manufacturer records;
      a manufacturer recall management module to manage and create a recall list having a plurality of recall notices;
      a manufacturer recall notice module that enables a manufacturer to send at least one of the plurality of recall notices to a physician and a hospital;
      a manufacturer acknowledgement module that allows the manufacturer to receive and store an acknowledge confirmation notice from the physician and the hospital in a sent recall acknowledge list;
      a recalled device tracking module that enables the implant manufacturer to view a location and the status of the plurality of implant devices related to a recall of the at least one implant device utilizing a device lot number;
      a manufacturer recall device alert module to receive an immediate notification of a recall status of the at least one implant device generated by the implant device tracking application at a time of an implant device scanning thereby preventing an implantation of a recalled implant device in a patient's body during a medical procedure;
      a manufacturer device placement module that allows the manufacturer to view a location of the at least one implant device in the patient's body;
      a manufacturer incoming message module configured to manage incoming messages from the at least one communication device;
      a manufacturer outgoing message module for creating and managing outgoing messages from the implant manufacturer; and
      a survey management module that performs at least one implant device survey;
   wherein the implant manufacturer access unit provides instructions for use (IFU) restrictions and requirements, recall notices and device information to the at least one of the plurality of implant devices;
   a hospital access unit including:
      a hospital incoming message module configured to manage incoming messages from the at least one communication device;

a hospital outgoing message module to manage an implant device communication section and the outgoing messages to the at least one communication device;

a hospital recall notice module that enables a hospital to receive the at least one of the plurality of recall notices from the implant manufacturer;

a hospital acknowledgement module that allows the hospital to send the acknowledge confirmation notice to the implant manufacturer;

a hospital recall forward module to forward the at least one of the plurality of recall notices to the patient;

a hospital device placement module that allows the hospital to view the location of the at least one implant device in the patient's body;

a hospital recall device alert module to receive the immediate notification of the recall status of the at least one implant device generated by the implant device tracking application at the time of the implant device scanning thereby preventing the implantation of the recalled implant device in the patient's body; and a procedure record access module to access at least one procedure record of the patient utilizing a searchable list of procedure records;

wherein the hospital access unit provides instructions for use (IFU) restrictions and requirements, recall notices and device information to the at least one of the plurality of implant devices;

a physician access unit including:
 a patient information module to view an existing patient record and to create a new patient record;
 a procedure record module to view an existing procedure record and to create a new procedure record;
 a device master data module to access records of the plurality of implant devices;
 a physician recall notice module that enables the physician to receive the at least one of the plurality of recall notices from the implant manufacturer;
 a physician acknowledgement module that allows the physician to send the acknowledge confirmation notice to the implant manufacturer;
 a physician device placement module that allows the physician to position an implant device icon on an image of the patient's body during a medical procedure thereby displaying the location of the at least one implant device on the patient's body;
 a physician recall device alert module to receive the immediate notification of the recall status of the at least one implant device generated by the implant device tracking application at the time of the implant device scanning thereby preventing the implantation of the recalled implant device in the patient's body;
 a physician incoming message module to inform the hospital appointment reminders and to indicate a status of each notice to the patient;
 a physician outgoing message module to manage outgoing messages and the implant device communication section; and
 an emergency physician contact module to store emergency contact details of the physician in the database unit;

wherein the physician access unit provides IFU restrictions and requirements, the recall notices, and the device information to the at least one of the plurality of implant devices; and a patient access unit including:
 a patient contact information module to store contact information of the patient in the database unit;
 a patient health check-up module to store a list of health checks and follow-up visit data in the database unit;
 a device ID card module to provide an electronic wallet of a medical device ID card to the patient that allows the patient to store medical device identification information of the patient in a password protected and traceable application;
 a patient recall module that enables the patient to receive the at least one of the plurality of recall notices forwarded by the physician and the hospital;
 a patient device placement module that allows the patient to view the location of the at least one implant device in the patient's body;
 a medical device procedure tracking module that enables the patient to access the device information, recall information, procedure notes, procedure images and the location of the implant device on the image of the patient body;
 a medical history module to store information regarding patient medical history, disease symptoms and medications in the database unit; and
 an emergency contact module for storing emergency contact details of the patient in the database unit;

wherein a patient access unit provides IFU restrictions and requirements, the recall notices, and the device information to the at least one of the plurality of implant devices;

whereby the hospital access unit, the implant manufacturer access unit, the patient access unit, and the physician access unit provide an efficient and consistent way to track the plurality of implant devices thereby improving the safety of the patient.

2. The system of claim 1 further comprising an acknowledgement message mechanism that allows the patient, the physician, the hospital, and the implant manufacturer to acknowledge a plurality of messages having immutable and traceable records.

3. The system of claim 1 wherein the at least one communication device is selected from a group consisting of: a cellular telephone, a smartphone, a wireless-enabled personal digital assistant, a tablet, a personal computer, a laptop and/or a mobile device.

4. The system of claim 1 wherein the network is a data communication network selected from at least one of but not limited to: Internet, a local area network (LAN), a wide area network (WAN), wired Ethernet, wireless Ethernet and cellular wireless network.

5. The system of claim 1 wherein the device ID card module in the patient access unit allows the patient to access the medical device ID card from anywhere and at any time as desired utilizing the password protected and traceable application.

6. The system of claim 1 wherein the recalled device tracking module in the implant manufacturer access unit displays a message status.

7. The system of claim 1 wherein the recall management module in the implant manufacturer access unit manages details regarding a placement of the at least one implant device in the patient's body and said recall information of the at least one implant device thereby enabling matching of the recalled implant device with the at least one implant device of the patient.

8. The system of claim 1 wherein a manufacturer procedure record access module in the implant manufacturer access unit enables to access at least one manufacturer procedure record of the patient.

9. The system of claim 1 wherein a survey result handling module in the implant manufacturer access unit allows the implant manufacturer to review survey responses from the at least one implant device survey.

10. The system of claim 1 wherein the implant manufacturer access unit includes a company information update module for updating information associated with the implant manufacturer.

11. The system of claim 1 wherein the hospital access unit includes a patient information access module configured to access patient information utilizing a searchable list of patients.

12. The system of claim 1 wherein a physician contact information module in the physician access unit stores contact information of the physician in the database unit.

13. The system of claim 1 wherein the physician access unit includes a physician health check-up module to store a list of health checks and follow-up visit data in the database unit.

14. The system of claim 1 wherein a physician information update module in the physician access unit updates contact information of the physician.

15. The system of claim 1 wherein a patient incoming notice module in the patient access unit informs hospital appointment reminders and the status of each notice to the patient.

16. A system for identifying and tracking a plurality of implant devices, the system comprising:
- at least one communication device operatively coupled with at least one of the plurality of implant devices; and
- a medical implant device tracking system in communication with the at least one communication device and the plurality of implant devices via a network, the medical implant device tracking system including an implant tracking server residing on a central computer having a processor on which is installed an implant device tracking application and coupled with a memory unit integrated with a central database, the implant device tracking application enables the at least one communication device to scan a unique device identifier (UDI) of the at least one of the plurality of implant devices thereby recording a complete and accurate information of the at least one of the plurality of implant devices, the medical implant device tracking system comprising:
  - a database unit configured to store and manage implant device information in an implant device database and logic to manage and route data to the at least one communication device;
  - an implant manufacturer access unit including:
    - a data collecting and reporting module to manage a plurality of manufacturer records;
    - a manufacturer recall management module to manage and create a recall list having a plurality of recall notices;
    - a manufacturer recall notice module that enables a manufacturer to send at least one of the plurality of recall notices to a physician and a hospital;
    - a manufacturer acknowledgement module that allows the manufacturer to receive and store an acknowledge confirmation notice from the physician and the hospital in a sent recall acknowledge list;
    - a recalled device tracking module that enables the implant manufacturer to view a location and the status of the plurality of implant devices related to a recall of the at least one implant device utilizing a device lot number;
    - a manufacturer recall device alert module that receives an immediate notification of a recall status of the at least one implant device generated by the implant device tracking application at a time of an implant device scanning and prevents an implantation of a recalled implant device in a patient's body during a medical procedure generated by the implant device tracking application;
    - a manufacturer device placement module that allows the manufacturer to view a location of the at least one implant device in the patient's body;
    - a manufacturer procedure record access module to access at least one manufacturer procedure record of a patient;
    - a manufacturer incoming message module configured to manage incoming messages from the at least one communication device;
    - a manufacturer outgoing message module for creating and managing outgoing messages from the implant manufacturer;
    - a survey management module performs at least one implant device survey; and
    - a company information update module for updating information associated with the implant manufacturer;
  - wherein the implant manufacturer access unit provides instructions for use (IFU) restrictions and requirements, recall notices and device information to the at least one of the plurality of implant devices;
  - a hospital access unit including:
    - a hospital incoming message module configured to manage incoming messages from the at least one communication device;
    - a hospital outgoing message module to manage an implant device communication section and the outgoing messages to the at least one communication device;
    - a hospital recall notice module that enables the hospital to receive the at least one of the plurality of recall notices from the implant manufacturer;
    - a hospital acknowledgement module that allows the hospital to send an acknowledge confirmation notice to the implant manufacturer;
    - a hospital recall forward module to forward the at least one of the plurality of recall notices to the patient;
    - a hospital device placement module that allows the hospital to view the location of the at least one implant device in the patient's body;
    - a hospital recall device alert module to receive the immediate notification of the recall status of the at least one implant device generated by the implant device tracking application at the time of the implant device scanning thereby preventing the implantation of the recalled implant device in the patient's body;

a patient information access module configured to access patient information utilizing a searchable list of patients; and a procedure record access module to access at least one procedure record of the patient utilizing a searchable list of procedure records;

wherein the hospital access unit provides instructions for use (IFU) restrictions and requirements, recall notices and device information to the at least one of the plurality of implant devices;

a physician access unit including:

a patient information module to view an existing patient record and to create a new patient record;

a procedure record module to view an existing procedure record and to create a new procedure record;

a device master data module to access records of the plurality of implant devices;

a physician recall notice module that enables the physician to receive the at least one of the plurality of recall notices from the implant manufacturer;

a physician acknowledgement module that allows the physician to send the acknowledge confirmation notice to the implant manufacturer;

a physician recall forward module to forward the at least one of the plurality of recall notices to the patient;

a physician device placement module that allows the physician to position an implant device icon on an image of the patient's body during a medical procedure thereby displaying the location of the at least one implant device on the patient's body;

a physician recall device alert module to receive the immediate notification of the recall status of the at least one implant device generated by the implant device tracking application at the time of the implant device scanning thereby preventing the implantation of the recalled implant device in the patient's body;

an emergency physician contact module for storing emergency contact details of the physician in the database unit;

a physician incoming message module to inform the hospital appointment reminders and to indicate a status of each notice to the physician;

a physician outgoing message module to manage outgoing messages and the implant device communication section; and a physician information update module to update contact information of the physician;

wherein the physician access unit provides IFU restrictions and requirements, the recall notices, and the device information to the at least one of the plurality of implant devices; and a patient access unit including:

a patient contact information module to store contact information of patients in the database unit;

a patient health check-up module to store a list of health checks and follow-up visit data in the database unit;

a device ID card module to provide an electronic wallet of a medical device ID card to the patient that allows the patient to store medical device identification information of the patient in a password protected and traceable application;

a patient recall module that enables the patient to receive the at least one of the plurality of recall notices forwarded by the physician and the hospital;

a patient device placement module that allows the patient to view the location of the at least one implant device in the patient's body;

a medical device procedure tracking module enables the patient to access the device information, recall information, procedure notes, procedure images and the location of the implant device on the image of the patient body;

a medical history module to store information regarding patient medical history, disease symptoms and medications in the database unit;

a patient incoming notice module to inform hospital appointment reminders and a status of each notice to the patient; and an emergency contact module for storing emergency contact details of the patient in the database unit;

wherein the patient access unit provides IFU restrictions and requirements, the recall notices, and the device information to the at least one of the plurality of implant devices;

whereby the hospital access unit, the implant manufacturer access unit, the patient access unit, and the physician access unit provide an efficient and consistent way to track the plurality of implant devices thereby improving the safety of the patient.

17. The system of claim 16 further comprising an acknowledgement message mechanism that allows the patient, the physician, the hospital, and the implant manufacturer to acknowledge a plurality of messages having immutable and traceable records.

18. The system of claim 16 wherein the physician access unit includes a physician contact information module for storing contact information of the physician in the database unit.

19. The system of claim 16 wherein a physician health check-up module in the physician access unit stores a list of health checks and follow-up visit data in the database unit.

20. A system comprising computer executable instructions embodied in a non-transitory computer readable storage medium having a computer readable program code embodied therein, the computer readable program code configured to be executed on a computer system to implement a method for creating and managing a plurality of recall notices utilizing a medical implant device tracking system via a network, the method comprising the steps of:

a. providing an implant device tracking application installed at a processor in the medical implant device tracking system being in communication with at least one communication device via a network;

b. enabling a manufacturer to select at least one implant device and a device lot number associated with the at least one implant device;

c. enabling the manufacturer to create at least one of the plurality of recall notices and attach a recall date to the at least one recall notice utilizing a manufacturer recall management module in an implant manufacturer access unit of the medical implant device tracking system;

d. searching for the device lot number for all procedures with said implant device in an implant device database connected to a hospital access unit, a physician access unit, and the implant manufacturer access unit;

e. automatically routing the at least one recall notice to a physician and a hospital utilizing a secured notification process in the medical implant device tracking system;
f. enabling the physician and the hospital to receive the at least one recall notice utilizing a physician recall notice module in the physician access unit and a hospital recall notice module in the hospital access unit;
g. enabling the physician and the hospital to send an acknowledge confirmation notice to the manufacturer utilizing a physician acknowledgement module and a hospital acknowledgement module;
h. enabling the manufacturer to receive the acknowledge confirmation notice in a sent recall acknowledge list utilizing a manufacturer acknowledgement module in the implant manufacturer access unit;
i. enabling the hospital and the physician to forward the at least one recall notice to at least one patient; and
j. enabling the implant device tracking application to automatically capture the at least one patient with the recalled device and the device lot number and automatically pushing the at least one recall notice to a patient access unit in the medical implant device tracking system.

* * * * *